United States Patent
Giles-Komar et al.

(10) Patent No.: US 7,291,721 B2
(45) Date of Patent: Nov. 6, 2007

(54) ANTI-IL-6 ANTIBODIES, COMPOSITIONS, METHODS AND USES

(75) Inventors: Jill Giles-Komar, Downingtown, PA (US); David Knight, Berwyn, PA (US); David Peritt, Bala Cynwyd, PA (US); Mohit Trikha, Paoli, PA (US)

(73) Assignee: Centocor, Inc., Malvern, PA (US)

( * ) Notice: Subject to any disclaimer, the term of this patent is extended or adjusted under 35 U.S.C. 154(b) by 484 days.

(21) Appl. No.: 10/280,716

(22) Filed: Oct. 26, 2002

(65) Prior Publication Data

US 2006/0188502 A1 Aug. 24, 2006

Related U.S. Application Data

(60) Provisional application No. 60/332,743, filed on Nov. 14, 2001.

(51) Int. Cl.
*C07H 21/04* (2006.01)
(52) U.S. Cl. .............................. 536/23.53; 435/320.1; 435/69.6
(58) Field of Classification Search ...................... None
See application file for complete search history.

(56) References Cited

U.S. PATENT DOCUMENTS

| | | | |
|---|---|---|---|
| 5,326,859 A | | 7/1994 | Sugano et al. |
| 5,468,609 A | | 11/1995 | Revel et al. |
| 5,530,101 A | * | 6/1996 | Queen et al. ............ 530/387.3 |
| 5,554,513 A | | 9/1996 | Revel et al. |
| 5,559,012 A | | 9/1996 | Brailly et al. |
| 5,591,827 A | | 1/1997 | Brakenhoff et al. |
| 5,618,700 A | | 4/1997 | Novick et al. |
| 5,618,920 A | * | 4/1997 | Robinson et al. ......... 530/387.1 |
| 5,639,455 A | | 6/1997 | Shimamura et al. |
| 5,723,120 A | | 3/1998 | Brakenhoff et al. |
| 5,789,552 A | | 8/1998 | Savino et al. |
| 5,807,715 A | * | 9/1998 | Morrison et al. .......... 435/69.6 |
| 5,849,283 A | | 12/1998 | Ciliberto |
| 5,854,398 A | | 12/1998 | Chang et al. |
| 5,856,135 A | | 1/1999 | Tsuchiya et al. |
| 5,888,510 A | | 3/1999 | Kishimoto et al. |
| 5,888,511 A | | 3/1999 | Shurkovich et al. |
| 5,914,106 A | | 6/1999 | Ciliberto |
| 5,942,220 A | | 8/1999 | Warren et al. |
| 5,958,400 A | | 9/1999 | Ruben et al. |
| 5,972,902 A | | 10/1999 | Ciliberto |
| 6,010,864 A | | 1/2000 | Hoeprich, Jr. |
| 6,086,874 A | | 7/2000 | Yoshida et al. |
| 6,121,423 A | | 9/2000 | Tsuchiya et al. |
| 6,261,560 B1 | | 7/2001 | Tsujinaka et al. |

FOREIGN PATENT DOCUMENTS

| EP | 800829 B1 | 10/1997 |
|---|---|---|
| WO | WO9108774 A1 | 6/1991 |
| WO | WO9409138 A1 | 4/1994 |

OTHER PUBLICATIONS

Paul, Fundamental Immunology, 3rd Edition, 1993, pp. 292-295, under the heading "Fv Structure and Diversity in Three Dimensions".*
Rudikoff et al, Proc. Natl. Acad. Sci. USA 1982 vol. 79: p. 1979.*
Cruse and Lewis, Illustrated Dictionary of Imunology, 1995, p. 19.*
Just P.J. Brakenhoff, Margaret Hart, Els R. De Groot, Franco Di Padova and Lucien A. Aarden, "Structure-Function Analysis of Human IL-6-Epitope Mapping of Neutralizing Monoclonal Antibodies with Amino-and Carboxyl-Terminal Detetion Mutants" The Journal of Immunology, vol. 145, 561-568 No. 2, Jul. 15, 1990, USA.
Just P.J. Brakenhoff, Els R. De Groot, Ron F. Evers, Hans Pannekoek & Lucien A. Aarden Molecular Cloning and Expression of Hybridoma Growth Factor in Escherichia Coli, The Journal of Immunology, vol. 139, 4116-4121, No. 12, Dec. 15, 1987 USA.
H.C.T. Van Zaanen, H. M. Lokhorst, L A. Aarden, H. J. A. M. Rensink, S. O. Warnaar, M. H. J. Van Oers, Blocking Interleukin-6 Activity with Chimeric Anti-IL6 Monoclonal A ntibodies in Multiple Myeloma: Effects on Soluble IL6 Receptor and Soluble gp130, Leukemia & Lymphoma vol. 31, 31 (5-6)pp. 551-558.
H.C.T. Van Zaane, R. P. Koopmans, L. A. Aarden, H. J. A.M. Rensink, J.M.L. Stouthard, S.O. Warnaar, H.M. Lokhorst and M.H. J. Van Oers Endogenous Interleukin 6 Production in Multiple Myeloma Patients Treated with Chimeric Monoclonal Anti-IL6 Antibodies Indicates the Existence of a Positive Feed-back Loop, J. Clin. Invest., The American Society for Clinical Investigation, Inc., vol. 98, No. 6, Sep. 1996, 1441-1448, The Netherlands.
H.C.T. Van Zaanen, H. M. Lokhorst, L. A. Aarden, H. J. A. M. Rensink, S. O. Warnaar, J. Van Der Leue, M. H. J. Van Oers, Chimaeric anti-Interleukin 6 monoclonal antibodies in the treatment of advanced multiple myeloma: a Phase I dose—escalating study, British Journal of Haematology (102,783-790, 1998.
Jose Baselga and John Mendelsohn "Receptor Blockage with Monoclonal Antibodies as Anti-Cancer Therapy," Pharmac Ther. vol. 64, pp. 127-154, 1994 Elsevier Science Ltd. Great Britain.
Matsuda, et al, Eur. Journal Immunol. 18:951-956 (1988).
Seidman, Jonathan, Peritt David, "A novel monoclonal antibody screening method using the Luminex-100™ microsphere system," J. Immunol. Methods 267: 165-171, 2002.
Josebaselga and John Mendelsohn "Receptor Blockage with Monoclonal Antibodies as Anti-Cancer Therapy," Pharmac Ther. vol. 64, pp. 127-154, 1994 Elsevier Science Ltd., Great Britain.
Orlandi et al, Cloning Immunoglobulin variable domains for expression by the polymerase chain reaction. Proc. Natl. Accad. Sci. USA, May 1989, vol. 86, pp. 3833-3837, especially p. 3835.

(Continued)

*Primary Examiner*—Misook Yu
*Assistant Examiner*—Mark Halvorson
(74) *Attorney, Agent, or Firm*—Kenneth J. Dow

(57) ABSTRACT

The present invention relates to at least one novel chimeric, humanized or CDR-grafted anti-IL-6 antibodies derived from the murine CLB-8 antibody, including isolated nucleic acids that encode at least one such anti-IL-6 antibody, vectors, host cells, transgenic animals or plants, and methods of making and using thereof, including therapeutic compositions, methods and devices.

9 Claims, 12 Drawing Sheets

OTHER PUBLICATIONS

Brakenhoff et al, "Epitope Mapping of Neutralizing Monoclonal Antibodies with Amino- and Carboxyl-Terminal Detetion Mutuants," Journal of Immunology, 1990, vol. 145, pp. 561-568, USA.

Sato, K. et al.: Humanization of an Anti-Human IL-Mouse Monoclonocal Antibody Glycosylated in its Heavy Chain Variable Region Human Antibodies and Hydridomas, vol. 7, No. 4, 1996, pp. 175-183 XP008041468.

Naka, T. et. al: "The Paradigm of IL-6: From Basic Science to Medicine" Arthritis Research, Current Science, London,, GB vol. 4, No. SuppL. 3, May 9, 2002, pp. S233-S242, XP009031052.

EP Supplementary Search Report dated Jul. 24, 2006 for EP Appl. No. 02784436.4.

R.V. Petrov, "Immunology," Medicine Publishers, 56-58 (1987), Russian Article and Engliish translation.

* cited by examiner

A. C433A

B. C434A

C. C435A
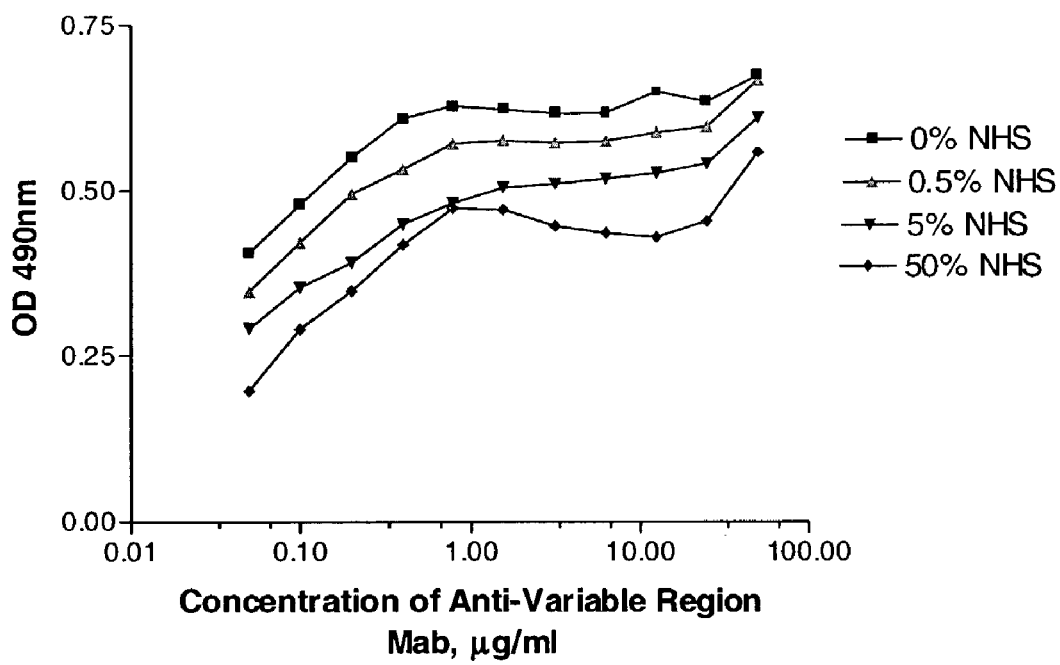
D. C436A
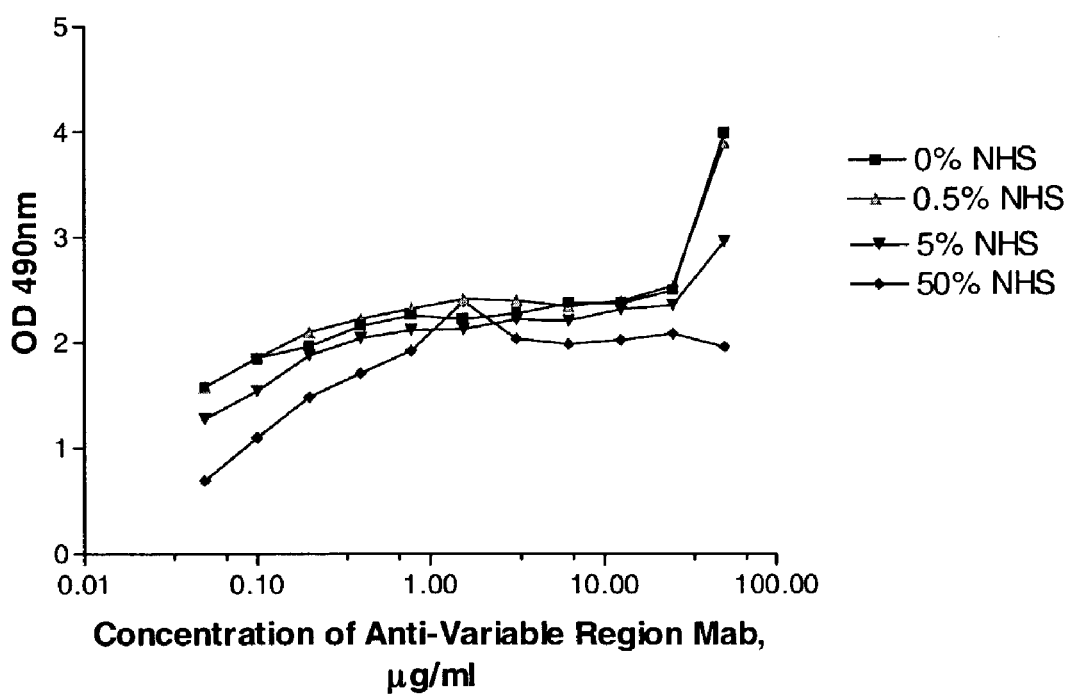

E. C437A
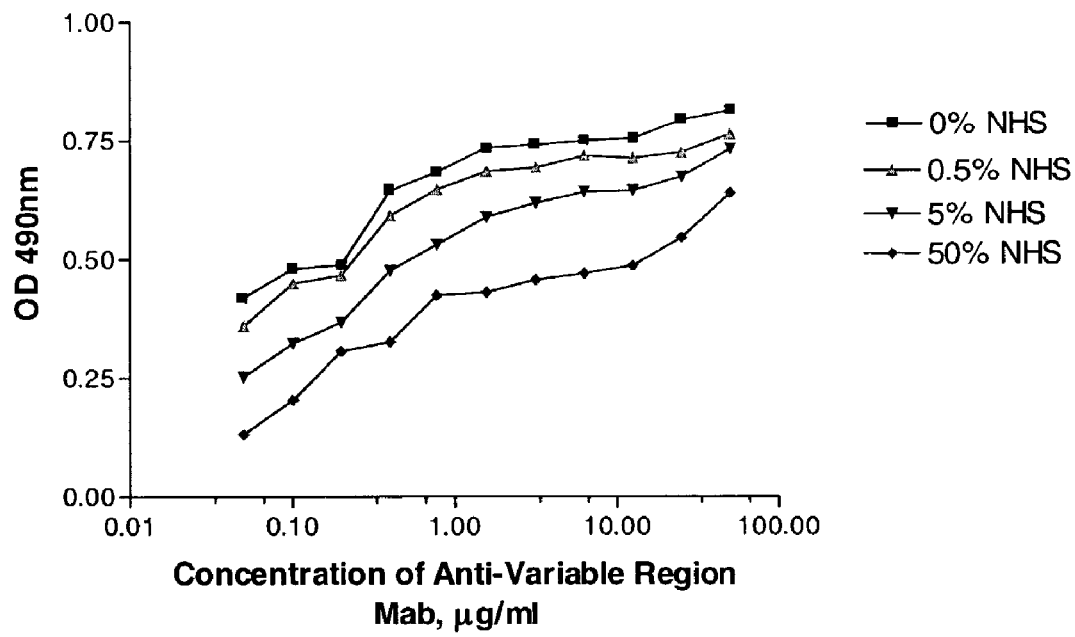
F. C438A
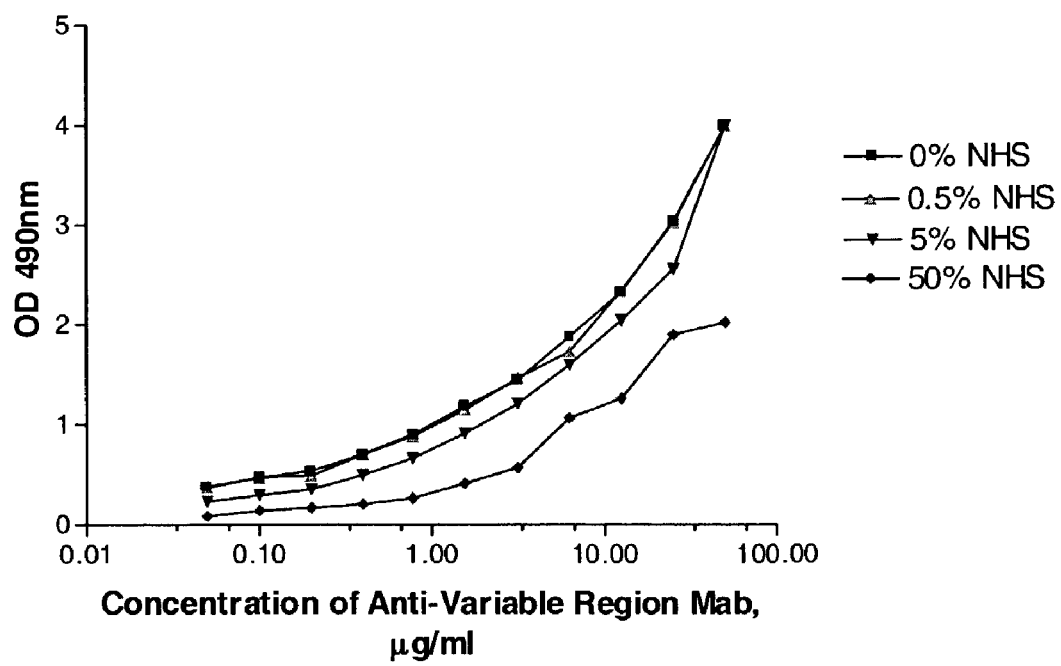

G. C439A
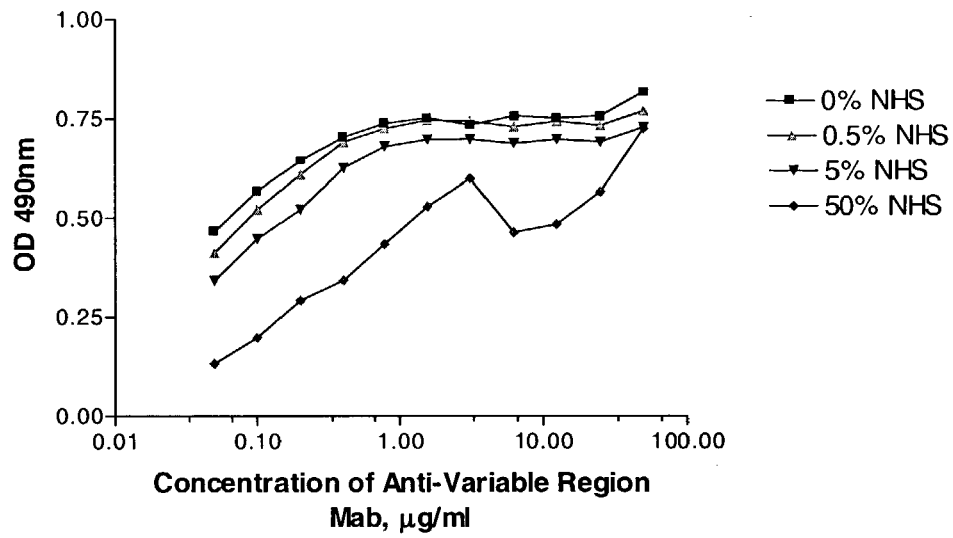
FIGURE 9
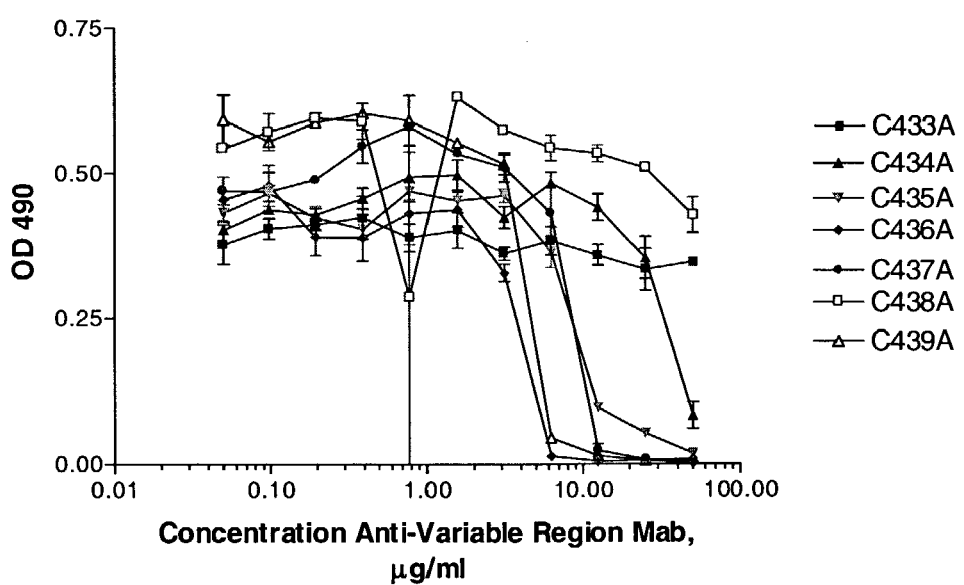

ANTI-IL-6 ANTIBODIES, COMPOSITIONS, METHODS AND USES

CROSS REFERENCE TO RELATED APPLICATION

This application claims the benefit of U.S. Provisional Application Ser. No. 60/332,743 filed Nov. 14, 2001, now abandoned.

BACKGROUND OF THE INVENTION

1. Field of the Invention

The present invention relates to antibodies, including specified portions or variants, specific for at least one Interleukin-6 (IL-6 also known as Interferon β2) protein or fragment thereof, as well as nucleic acids encoding such anti-IL-6 antibodies, complementary nucleic acids, vectors, host cells, and methods of making and using thereof, including therapeutic formulations, administration and devices.

2. Related Art

Interleukin-6 (IL-6) is a pro-inflammatory cytokine that is produced by many different cell types. In vivo, stimulated monocytes, fibroblasts, and endothelial cells represent the main sources of IL-6. Other cells such as macrophages, T and B lymphocytes, granulocytes, keratinocytes, mast cells, osteoblasts, chrondrocytes, glial cells, and smooth muscle cells also produce IL-6 after stimulation (Kishimoto, T., Blood 74:1–10 (1989) and Kurihara, N. et al., J. Immunology 144:4226–4230 (1990)). Several tumor cells also produce IL-6 (Smith, P. C. et al. Cytokine and Growth Factor Reviews 12:33–40 (2001)) and recently IL-6 was indicated to be a prognostic factor for prostate cancer progression (Nakashima, J. et al. Clinical Cancer Research 6:2702–2706 (2000)). IL-6 production can be regulated by IL-6 itself and depending upon cell type, IL-6 can stimulate or inhibit its own synthesis.

IL-6 can bind to the IL-6 receptor expressed on mitogen-activated B cells, T cells, peripheral monocytes, and certain tumors (Ishimi, Y. et al., J. Immunology 145:3297–3303 (1990)). The IL-6 receptor has at least two different components and is composed of an alpha chain called gp80 that is responsible for IL-6 binding and a beta chain designated gp130 that is needed for signal transduction (Adebanjo, O. et al., J. Cell Biology 142:1347–1356 (1998) and Poli, V. et al., EMBO 13:1189–1196 (1994)). The cytokine family which includes IL-6, LIF, Oncostatin M, IL-11, CNTF, and CT-1 all signal through gp130 after binding to their cognate receptors. In addition, all members of the IL-6 cytokine family can induce hepatic expression of acute phase proteins (Bellido, T. et al., J. Clin. Investigation 97:431–437 (1996)). 87908790.

There are at least two major biological functions of IL-6: mediation of acute phase proteins and acting as a differentiation and activation factor (Avvisti, G. et al., Baillieres Clinical Hematology 8:815–829 (1995) and Poli, V. et al., EMBO 13:1189–1196 (1994)). Acute phase proteins are known to regulate immune responses, mediate inflammation, and play a role in tissue remodeling. As a differentiation and activation factor, IL-6 induces B cells to differentiate and secrete antibody, it induces T cells to differentiate into cytotoxic T cells, activates cell signaling factors, and promotes hematopoiesis (Ishimi, Y. et al., J. Immunology 145: 3297–3303 (1990)). IL-6 is prominently involved in many critical bodily functions and processes. As a result, physiological processes including bone metabolism, neoplastic transformation, and immune and inflammatory responses can be enhanced, suppressed, or prevented by manipulation of the biological activity of IL-6 in vivo by means of an antibody (Adebanjo, O. et al., J. Cell Biology 142:1347–1356 (1998)).

Although IL-6 is involved in many pathways, IL-6 knock-out mice have a normal phenotype, they are viable and fertile, and these animals show slightly decreased number of T cells and decreased acute phase protein response to tissue injury (Kopf M et al., Impaired immune and acute-phase responses in interleukin-6-deficient mice, Nature; 368(6469):339–42, 1994). In contrast, transgenic mice that over-express IL-6 develop neurologic disease such as neurodegeneration, astrocytosis, cerebral vasculogenesis, and these mice do not develop a blood brain barrier (Campbell et al., Neurologic Disease Induced in Transgenic Mice by Cerebral Overexpression of Interleukin 6 PNAS 90: 10061–10065. 1993).

Recent studies have indicated that a Mab to IL-6 can inhibit in vivo growth of prostate tumors (Smith, P. C. and Keller, E. T., The Prostate in press and Okamoto, M. et al., Cancer Research 57:141–146 (1997) and renal carcinoma (Weissglas, M. et al., The Journal of Urology 153:554–557 (1995)). In addition to a direct effect on tumor growth, blocking IL-6 production can also chemo-sensitize and enhance cytotoxic efficacy (Smith, P. C. et al. Cytokine and Growth Factor Reviews 12:33–40 (2001)). Collectively, literature teaches us that blocking IL-6 activity can inhibit bone degradation, tumor growth and cancer cachexia.

Passive immunotherapy employing non-human, polyclonal (e.g., anti-sera) or monoclonal antibodies (Mabs) and fragments thereof (e.g., proteolytic digestion products thereof) are potential therapeutic agents that are being developed as treatments for various diseases. However, antibodies composed of non-human portions are known to elicit an immune response when administered to humans. This immune response makes repeated antibody administration often unsuitable for therapy and may result in an immune complex mediated clearance of the antibodies from circulation, thus reducing the therapeutic benefit to the patients. Examples of conditions that may be attributed to repeat administration of antibodies composed of non-human portions are serum sickness and anaphylaxis.

In an attempt to avoid these and other problems, a number of approaches including chimerization and "humanization" have been pursued to reduce the immunogenicity of the antibodies/fragments thereof. These approaches have produced antibodies having reduced immunogenicity. These antibodies are substantially of human origin, with only the complementary determing regions (CDR's) and certain framework residue that influence CDR conformation being of non human original. Novel human or humanized monoclonal antibodies are therefore particularly useful alone or in combination with existing molecules for immunotherapeutic uses.

Accordingly, there is a need to provide a high affinity, neutralizing chimeric or human antibodies to IL-6 or fragments thereof that overcome one more of these problems, as well as improvements over known antibodies or fragments thereof for use in preventing, treating, ameliorating, or diagnosing conditions related to the IL-6.

Murine monocolonal antibodies to IL-6 produced from a hybridoma cell line are known for example in U.S. Pat. No. 5,618,700. U.S. Pat. No. 5,856,135 discloses reshaped human antibodies to human IL-6 drived from a mouse monoclonal antibody SK2 in which the complementary determining regions (CDR's) from the variable region of the mouse antibody SK2 are transplanted into the variable region of a human antibody and joined to the constant region of a human antibody.

Other murine monoclonal antibodies have been described and categorized as neutralizing, that is preventing receptor binding, or non-neutralizing (Brakenhoff et al, J. Immunol. (1990) (145:561). Among this set of antibodies, neutralizing monoclonal antibodies to IL-6 can be divided into two groups; and the putative epitopes on the IL-6 molecule designated Site I and Site II. Site I prevent binding to the gp80 (IL6R) and therefore prevent gp130 activation. The Site I epitope was further characterized as comprising regions of both amino terminal and carboxy terminal portions of the IL-6 molecule. Site II binders prevent gp130 activation and therefore may recognize a conformational epitope involved in signalling.

A murine IL-6 monoclonal antibody referred to as CLB-6/8 or CLB-8, which has high affinity for IL-6, binds to the Site I epitope, is known (Brakenhoff et al supra), but the antigen binding domains (CDR regions) of this antibody are not known. As described above, however, the murine antibody is highly immunogenic in humans and its therapeutic value is therefore limited. There is thus a continuing need for antibodies to IL-6 that exhibit high affinity and a favorable pharmaceutical profile.

SUMMARY OF THE INVENTION

The present invention provides isolated chimeric, humanized and/or CDR-grafted anti-IL-6 antibodies, having at least one antigen binding region derived from the high affinity CLB-8 anti-IL-6 antibody, as well as anti-IL-6 antibody compositions, encoding or complementary nucleic acids, vectors, host cells, compositions, formulations, devices, transgenic animals, transgenic plants related thereto, and methods of making and using thereof, as described and enabled herein, in combination with what is known in the art. The antibody of the invention specifically neutralizes human IL-6 with high affinity.

The present invention provides at least one isolated human-mouse chimeric, humanized or CDR-grafted anti-IL-6 CLB-8 antibody ("cCLB-8 antibody") as described herein. The cCLB-8 antibody according to the present invention includes any protein or peptide molecule that comprises at least one complementarity determining region (CDR) of a heavy or light chain or a ligand binding portion thereof, derived from the murine CLB-8 monoclonal antibody, in combination with a heavy chain or light chain constant region, a framework region, or any portion thereof, that can be incorporated into an antibody of the present invention. In one embodiment the invention is directed to an anti-IL-6 chimeric antibody comprising two light chains and two heavy chains, each of the chains comprising at least part of a human constant region and at least part of a variable region (v) derived from the murine CLB8 monoclonal antibody having specificity to human IL-6, said antibody binding with high affinity to an inhibiting and/or neutralizing epitope of human IL-6, such as the antibody cCLB-8. The invention also includes fragments or a derivative of such an antibody, such as one or more portions of the antibody chain, such as the heavy chain constant, joining, diversity or variable regions, or the light chain constant, joining or variable regions.

The antibody can comprise at least one specified portion of at least one complementarity determining region (CDR) (e.g., CDR1, CDR2 or CDR3 of the heavy or light chain variable region) derived from the murine CLB-8 monoclonal antibody, and/or at least one constant or variable framework region or any portion thereof. The antibody amino acid sequence can further optionally comprise at least one specified substitution, insertion or deletion as described herein or as known in the art.

Preferred antibodies of the present invention include those chimeric, humanized and/or CDR grafted antibodies that will competitively inhibit in vivo binding to human IL-6 of anti-IL-6 murine CLB-8, chimeric anti-IL-6 CLB-8, or an antibody having substantially the same binding characteristics, as well as fragments and regions thereof.

Preferred antibodies of the present invention are those that bind epitopes recognized by CLB-8 and cCLB-8, which are included in the Site Iepitope as described by Brackenhoff et al. (supra). Preferred methods for determining monoclonal antibody specificity and affinity by competitive inhibition can be found in Harlow, et al, Antibodies: A Laboratory Manual, Cold Spring Harbor Laboratory Press, Cold Spring Harbor, N.Y., 1988), hereby incorporated by reference into the present application. At least one antibody of the invention binds at least one specified epitope specific to human IL-6 protein, subunit, fragment, portion or any combination thereof, to which the CLB-8 monoclonal antibody binds. The epitope can comprise at least one antibody binding region to which the CLB-8 antibody binds, which epitope is preferably comprised of at least 1–5 amino acids of at least one portion thereof, such as but not limited to, at least one functional, extracellular, soluble, hydrophillic, external or cytoplasmic domain of human IL-6 protein, or any portion thereof.

In one aspect, the present invention provides at least one isolated mammalian anti-IL-6 cCLB-8 antibody, comprising at least one variable region comprising SEQ ID NO:7 or 8 and the nucleic acid sequences encoding them (SEQ ID NO: 15 or 16).

In another aspect, the present invention provides at least one isolated mammalian anti-IL-6 cCLB-8 antibody, comprising either (i) all of the heavy chain complementarity determining regions (CDR) amino acid sequences of SEQ ID NOS:1, 2, and 3 and the nucleic acid sequences encoding them (SEQ ID NOS: 9–11); or (ii) all of the light chain CDR amino acids sequences of SEQ ID NOS:4, 5, and 6 and the nucleic acid sequences encoding them (SEQ ID NOS: 12–14).

In another aspect, the present invention provides at least one isolated mammalian anti-IL-6 cCLB-8 antibody, comprising at least one heavy chain or light chain CDR having the amino acid sequence of at least one of SEQ ID NOS: 1, 2, 3, 4, 5, or 6 and the nucleic acid sequences encoding them (SEQ ID NOS: 9–14).

In other aspect the present invention provides at least one isolated mammalian chimeric, humanized or CDR-grafted anti-IL-6 cCLB-8 antibody, comprising at least one human CDR, wherein the antibody specifically binds at least one epitope comprising at least 1-3 amino acids of the epitope of human IL-6 to which the CLB-8 antibody binds.

The at least one antibody can optionally further bind IL-6 with an affinity ($K_d$) of at least $10^{-9}$ M, preferably at least $10^{-10}$ M, and/or substantially neutralize at least one activity of at least one IL-6 protein. In a preferred embodiment, the antibody binds IL-6 with an affinity ($K_d$) of at least $1 \times 10^{-11}$ M, preferably $5 \times 10^{-11}$ neutralizes human IL-6.

The present invention provides, in one aspect, isolated nucleic acid molecules comprising, complementary, or hybridizing to, a polynucleotide encoding the aforementioned specific anti-IL-6 antibodies, comprising at least one specified sequence, domain, portion or variant thereof. The present invention further provides recombinant vectors comprising said anti-IL-6 antibody nucleic acid molecules, host cells containing such nucleic acids and/or recombinant vectors, as well as methods of making and/or using such antibody nucleic acids, vectors and/or host cells. Thus, the invention comprisesn isolated nucleic acid encoding at least one isolated mammalian anti-IL-6 cCLB-8 antibody; an isolated nucleic acid vector comprising the isolated nucleic acid, and/or a prokaryotic or eukaryotic host cell comprising the isolated nucleic acid. The host cell can optionally be at least one selected from COS-1, COS-7, HEK293, BHK21, CHO, BSC-1, Hep G2, 653, SP2/0, 293, HeLa, myeloma, or lymphoma cells, or any derivative, immortalized or transformed cell thereof. Also provided is a method for producing at least one anti-IL-6 cCLB-8 antibody, comprising translating the antibody encoding nucleic acid under conditions in vitro, in vivo or in situ, such that the IL-6 antibody is expressed in detectable or recoverable amounts.

The present invention further provides at least one IL-6 anti-idiotype antibody to at least one cCLB-8 anti-IL-6 antibody of the present invention. The anti-idiotype antibody includes any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework region, or any portion thereof, that can be incorporated into an anti-idiotype antibody to the antibody of the present invention. An anti-idiotype antibody of the invention can include or be derived from any mammal, such as but not limited to a human, a mouse, a rabbit, a rodent, a primate, and the like.

The present invention provides, in one aspect, isolated nucleic acid molecules comprising, complementary, or hybridizing to, a polynucleotide encoding at least one IL-6 anti-idiotype antibody, comprising at least one specified sequence, domain, portion or variant thereof. The present invention further provides recombinant vectors comprising said IL-6 anti-idiotype antibody encoding nucleic acid molecules, host cells containing such nucleic acids and/or recombinant vectors, as well as methods of making and/or using such anti-idiotype antiobody nucleic acids, vectors and/or host cells.

The present invention also provides at least one method for expressing at least one aforementioned anti-IL-6 antibody, or IL-6 anti-idiotype antibody in a host cell, comprising culturing a host cell as described herein under conditions wherein at least one anti-IL-6 antibody is expressed in detectable and/or recoverable amounts.

Also provided is a method for producing at least one isolated anti-IL-6 antibody of the present invention, comprising providing a transgenic animal or transgenic plant or plant cell capable of expressing the antibody in recoverable amounts. Further provided in the present invention is at least one anti-IL-6 antibody produced by the above method.

The present invention also provides at least one composition comprising (a) an isolated anti-IL-6 cCLB-8 antibody encoding nucleic acid and/or antibody as described herein; and (b) a suitable carrier or diluent. The carrier or diluent can optionally be pharmaceutically acceptable, according to known carriers or diluents. The composition can optionally further comprise at least one further compound, protein or composition.

The present invention further provides at least one anti-IL-6 cCLB-8 antibody method or composition, for administering a therapeutically effective amount to modulate or treat at least one IL-6 related condition in a cell, tissue, organ, animal or patient and/or, prior to, subsequent to, or during a related condition, as known in the art and/or as described herein. Thus, the invention provides a method for diagnosing or treating an IL-6 related condition in a cell, tissue, organ or animal, comprising contacting or administering a composition comprising an effective amount of at least one isolated anti-IL-6 cCLB-8 antibody of the invention with, or to, the cell, tissue, organ or animal. The method can optionally further comprise using an effective amount of 0.001–50 mg/kilogram of the cells, tissue, organ or animal. The method can optionally further comprise using the contacting or the administrating by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal. The method can optionally further comprise administering, prior, concurrently, or after the antibody contacting or administering at least one composition comprising an effective amount of at least one compound or protein selected from at least one of a detectable label or reporter, a TNF antagonist, an antirheumatic, a muscle relaxant, a narcotic, a non-steroid anti-inflammatory drug (NSAID), an analgesic, an anesthetic, a sedative, a local anesthetic, a neuromsucula-r blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog thereof, a cytotoxic or other anti-cancer agent, an anti-metabolite such as methotrexate, an anti-proliferative agent, a cytokine, or a cytokine antagonist.

The present invention further provides at least one anti-IL-6 cCLB-8 antibody method for diagnosing at least one IL-6 related condition in a cell, tissue, organ, animal or patient and/or, prior to, subsequent to, or during a related condition, as known in the art and/or as described herein.

The present invention also provides at least one composition, device and/or method of delivery for diagnosing of at least one anti-IL-6 antibody, according to the present invention.

Also provided is a composition comprising at least one isolated chimeric, human or humanized anti-IL-6 cCLB-8 antibody and at least one pharmaceutically acceptable carrier or diluent. The composition can optionally further comprise an effective amount of at least one compound or protein selected from at least one of a detectable label or reporter, a cytotoxic or other anti-cancer agent, an anti-metabolite such as methotrexate, an anti-proliferative agent, a cytokine, or a cytokine antagonist, a TNF antagonist, an antirheumatic, a muscle relaxant, a narcotic, a non-steroid anti-inflammatory drug (NTHE), an analgesic, an anesthetic, a sedative, a local anethetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog.

Also provided is a medical device, comprising at least one isolated mammalian anti-IL-6 antibody of the invention, wherein the device is suitable to contacting or administering the at least one anti-IL-6 antibody by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal.

Also provided is an article of manufacture for human pharmaceutical or diagnostic use, comprising packaging material and a container comprising a solution or a lyophilized form of at least one isolated mammalian anti-IL-6 antibody of the present invention. The article of manufacture can optionally comprise having the container as a component of a parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal delivery device or system.

The present invention further provides any invention described herein.

DESCRIPTION OF THE FIGURES

FIG. 9: Graph showing the inhibition of cCLB8 binding to human IL-6 by anti-id Mabs.

DETAILED DESCRIPTION OF THE INVENTION

Citations

Figure 1:
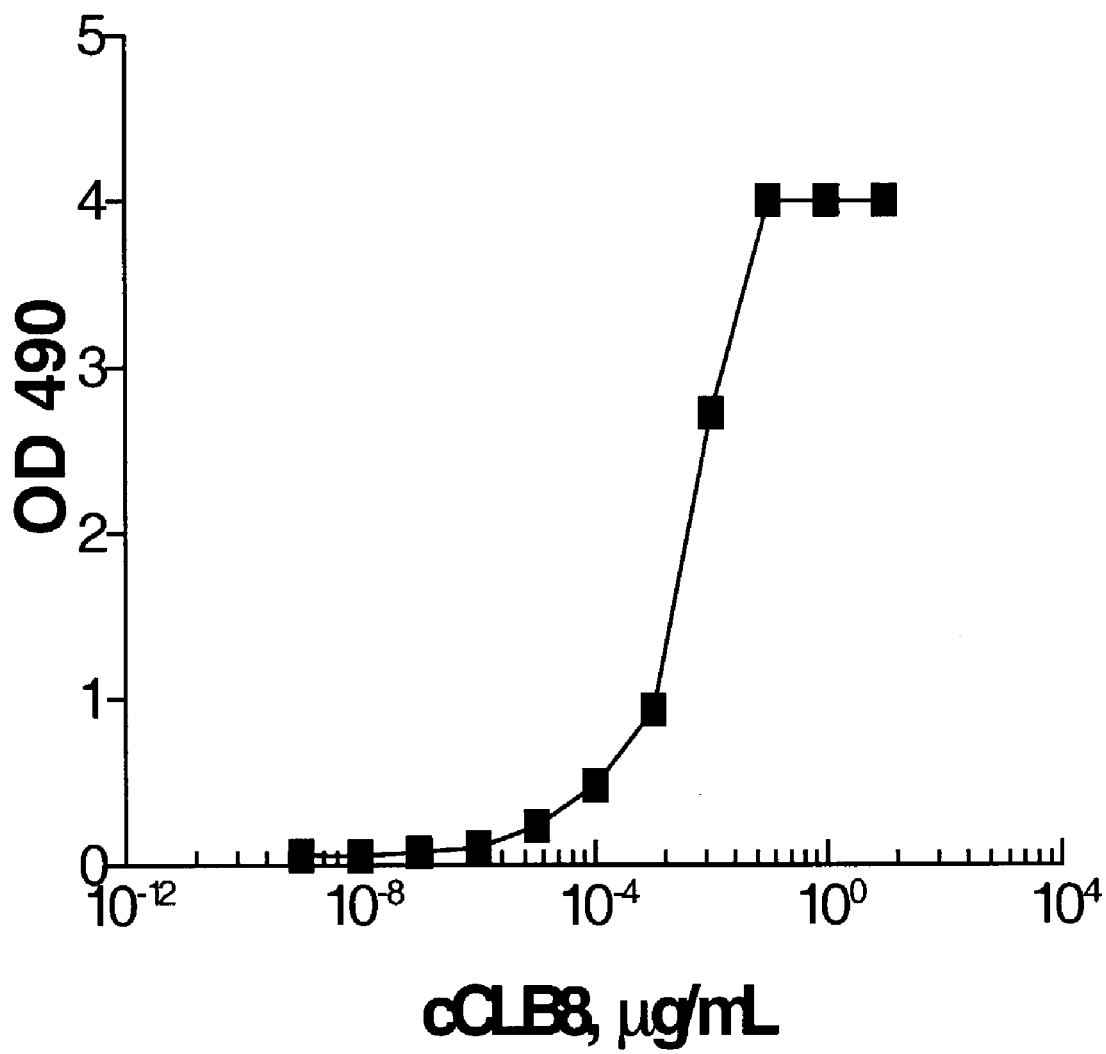
FIG. 1: Graph showing binding of cCLB8 to human recombinant IL-6.

All publications or patents cited herein are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, N.Y. (1987–2001); Sambrook, et al., Molecular Cloning: A Laboratory Manual, $2^{nd}$ Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994–2001); Colligan et al., Current Protocols in Protein Science, John Wiley & Sons, NY, N.Y., (1997–2001).

Amino Acid Codes

The amino acids that make up anti-IL-6 antibodies of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994):

Definitions

As used herein, an "anti-Interleukin-6 cCLB-8 antibody," "anti-IL-6 cCLB-8 antibody," "anti-IL-6 cCLB-8 antibody portion," or "anti-IL-6 cCLB-8 antibody fragment" and/or "anti-IL-6 cCLB-8 antibody variant" and the like include any protein or peptide containing molecule that comprises at least a portion of an immunoglobulin molecule, containing at least one complementarity determining region (CDR) of a heavy or light chain or a ligand binding portion thereof derived from the murine CLB-8 monoclonal antibody in combination with a heavy chain or light chain variable region, a heavy chain or light chain constant region, a framework region, or any portion thereof, of non-murine origin, preferably of human origen, which can be incorporated into an antibody of the present invention. Such antibody is capable of modulating, decreasing, antagonizes, mitigates, aleviates, blocks, inhibits, abrogates and/or interferes with at least one IL-6 activity or binding, or with IL-6 receptor activity or binding, in vitro, in situ and/or in vivo. As a non-limiting example, a suitable anti-IL-6 antibody, specified portion or variant of the present invention can bind with high affinity to an inhibiting and/or neutralizing epitope of human IL-6 recognized by the CLB-8 monoclonal antibody. A suitable anti-IL-6 antibody, specified portion, or variant can also optionally affect at least one of IL-6 activity or function, such as but not limited to, RNA, DNA or protein synthesis, IL-6 release, IL-6 receptor signaling, membrane IL-6 cleavage, IL-6 activity, IL-6 production and/or synthesis.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof; each containing at least one CDR derived from the CLB-8 monoclonal antibody. Functional fragments include antigen-binding fragments that bind to a mammalian IL-6. For example, antibody fragments capable of binding to IL-6 or portions thereof, including, but not limited to Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the CH$_1$ domain and/or hinge region of the heavy chain. The various portions of antibodies can be joined together chemically by conventional techniques, or can be prepared as a contiguous protein using genetic engineering techniques.

As used herein "chimeric" antibodies or "humanized" antibodies or "CDR-grafted" include any combination of the herein described murine CDR's with one or more proteins or peptides derived from a non-murine, preferably, human antibody. In accordance with the invention, chimeric or humanized antibodies are provided wherein the CDR's are derived from the murine CLB-8 antibody capable of binding human IL-6 and at least a portion, or the remainder of the antibody is derived from one or more human antibodies. Thus, the human part of the antibody may include the framework, C$_L$, C$_H$ domains (e.g., C$_H$1, C$_H$2, C$_H$3), hinge, (V$_L$, V$_H$)) regions which are substantially non-immunogenic in humans. The regions of the antibody that are derived from human antibodies need not have 100% identity with human antibodies. In a preferred embodiment, as many of the human amino acid residues as possible are retained in order for the immunogenicity to be negligible, but the human residues may be modified as necessary to support the antigen binding site formed by the CDR's while simultaneously maximizing the humanization of the antibody. Such changes or variations optionally and preferably retain or reduce the immunogenicity in humans or other species relative to non-modified antibodies. It is pointed out that a humanized antibody can be produced by a non-human animal or prokaryotic or eukaryotic cell that is capable of expressing functionally rearranged human immunoglobulin (e.g., heavy chain and/or light chain) genes. Further, when the antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Antibodies of the Present Invention

In accordance with the present invention, the anti-IL-6 cCLB-8 antibody comprises an antibody in which the variable region or CDRs are derived from the murine CLB-8 antibody capable of binding to and inhibiting the function of human IL-6 and the framework and constant regions of the antibody are derived from one or more human antibodies. The variable region or CDRs derived from the murine CLB-8 antibody preferably have from about 90% to about 100% identity with the variable region or CDRs of the murine CLB-8 antibody, although any and all modifications, including substitutions, insertions and deletions, are contemplated so long as the chimeric antibody maintains the ability to bind to and inhibit IL-6. The regions of the chimeric, humanized or CDR-grafted antibodies that are derived from human antibodies need not have 100% identity with the human antibodies. In a preferred embodiment, as many of the human amino acid residues as possible are retained in order than immunogenicity is negligible, but the human residues, in particular residues of the framework region, are substituted as required and as taught hereinbelow in accordance with the present invention. Such modifications as disclosed herein are necessary to support the antigen binding site formed by the CDRs while sumultaneously maximizing the humanization of the antibody.

The CLB-8 murine monoclonal antibody against human IL-6 is known in the art (Brakenhoff et al, supra), but the CDR regions of this antibody have not heretofore been disclosed. The present invention, for the first time, discloses chimeric, humanized or CDR grafted antibodies derived from the CDR regions of the CLB-8 murine monoclonal antibody and methods for preparing such antibodies. In accordance with the present invention, the cDNA (SEQ ID NO: 15) and amino acid sequences of the heavy chain (SEQ ID NO: 7) of murine CLB-8 heavy chain is provided at Example 2. The cDNA and deduced amino acid sequence of the murine CLB-8 light chain (SEQ ID NO: 8) is also provided in Example 2 (SEQ ID NO: 16). Each of the heavy and light chain variable regions contain three CDRs that combine to form the antigen binding site. The three CDRs are surrounded by four FR regions that primarily function to support the CDRs. The sequences of the CDRs within the sequences of the variable regions of the heavy and light chains can be identified by computer-assisted alignment according to Kabat et al. (1987) in Sequences of Proteins of Immunological Interest, 4$^{th}$ ed., United States Department of Health and Human Services, U.S. Government Printing Office, Washington, D.C., or by molecular modeling of the variable regions, for example utilizing the ENCAD program as described by Levitt (1983) J. Mol. Biol. 168:595.

In a preferred embodiment the CDRs are derived from murine monoclonal antibody CLB-8. The preferred heavy chain CDRs have the following sequences:

```
CDR1    SFAMS              (SEQ ID NO:1)
CDR2    EISSGGSYTYYPDTVTG  (SEQ ID NO:2)
CDR3    GLWGYYALDY         (SEQ ID NO:3)
```

The preferred light chain CDRs have the following sequences:

```
CDR1    SASSSVSYMY    (SEQ. ID NO:4)
CDR2    DTSNLAS       (SEQ. ID NO:5)
CDR3    QQWSGYPYT     (SEQ. ID NO:6)
```

The sequences of the CDRs of the murine CLB-8 antibody, may be modified by insertions, substitutions and deletions to the extent that the CDR-grafted antibody maintains the ability to bind to and inhibit human Il-6. The ordinarily skilled artisan can ascertain the maintenance of this activity by performing the functional assays described hereinbelow. The CDRs can have, for example, from about 50% to about 100% homology to the CDRs of SEQ ID NOS: 1–6. In a preferred embodiment the CDRs have from about 80% to about 100% homology to the CDRs of SEQ ID NOS: 1–6. In a more preferred embodiment the CDRs have from about 90% to about 100% homology to the CDRs of SEQ ID NOS: 1–6. In a most preferred embodiment the CDRs have from about 100% homology to the CDRs of SEQ ID NOS: 1–6.

Alternatively, the entire heavy chain variable region and light chain variable region of the murine CLB-8 antibody as set forth in Example 2 (SEQ ID NOS. 7 and 8) may be combined with the human constant and framework regions to form the chimeric cCLB-8 antibody of the present invention.

Human genes which encode the constant (C) regions of the chimeric antibodies, fragments and regions of the present invention can be derived from a human fetal liver library, by known methods. Human C region genes can be derived from any human cell including those which express and produce human immunoglobulins. The human $C_H$ region can be derived from any of the known classes or isotypes of human H chains, including gamma, μ, α, δ, ε, and subtypes thereof, such as G1, G2, G3 and G4. Since the H chain isotype is responsible for the various effector functions of an antibody, the choice of CH region will be guided by the desired effector functions, such as complement fixation, or activity in antibody-dependent cellular cytotoxicity (ADCC). Preferably, the CH region is derived from gamma 1 (IgG1).

The human $C_L$ region can be derived from either human L chain isotype, kappa or lambda, preferably kappa.

Genes encoding human immunoglobulin C regions are obtained from human cells by standard cloning techniques (Sambrook, et al. (*Molecular Cloning: A Laboratory Manual*, $2^{nd}$ Edition, Cold Spring Harbor Press, Cold Spring Harbor, N.Y. (1989) and Ausubel et al, eds. *Current Protocols in Molecular Biology* (1987–1993)). Human C region genes are readily available from known clones containing genes representing the two classes of L chains, the five classses of H chains and subclasses thereof. Chimeric antibody fragments, such as $F(ab^1)_2$ and Fab, can be prepared by designing a chimeric H chain gene which is appropriately truncated. For example, a chimeric gene encoding an H chain portion of an $F(ab^1)_2$ fragment would include DNA sequenes encoding the CH1 domain and hinge region of the H chain, followed by a translational stop codon to yield the truncated molecule.

Generally, in one example, chimeric antibodies, fragments and regions of the present invention are produced by cloning DNA segments encoding the H and L chain antigen-binding regions of the CLB-8 anti IL-6 specific antibody, and joining these DNA segments to DNA segments encloding $C_H$ and $C_L$ regions, respectively, to produce chimeric immunoglobulin-encoding genes.

Thus, in a preferred embodiment, a fused chimeric gene is created which comprises a first DNA segment that encodes at least the antigen-binding region of non-human origin, such as a functionally rearranged V region with joining (J) segment, linked to a second DNA segment encoding at least a part of a human C region.

The sequences of the variable regions of the murine CLB-8 antibody, may be modified by insertions, substitutions and deletions to the extent that the chimeric antibody maintains the ability to bind to and inhibit human IL-6. The ordinarily skilled artisan can ascertain the maintenance of this activity by performing the functional assays described hereinbelow. The variable regions can have, for example, from about 50% to about 100% homology to the variable regions of SEQ ID NOS:7–8. in a preferred embodiment the variable regions have from about 80% to about 100% homology to the variable regions of SEQ ID NOS: 7–8. In a more preferred embodiment the variable regions have from about 90% to about 100% homology to the variable regions of SEQ ID NOS: 7–8. In a most preferred embodiment the variable regions have from about 100% homology to the CDRs of SEQ ID NOS: 1–6.

For convenience, the numering scheme of Kabat et al., has been adopted herein. Residues are designated by lower case numbers or hyphens as necessary to conform the present sequences to the standard Kabat numbered sequence.

In accordance with the present invention, in the case of a CDR-grafted or humanized antibody where the CDR region of the CLB-8 antibody is combined with a human region, residues may be retained in the FR region which are idiosyncratic to the parent antibody, e.g. CLB-8. Residues that have been demonstrated to be critical in the humanization of other antibodies may also be retained. The foregoing guidelines are followed to the extent necessary to support the antigen binding site formed by the CDRs while simultaneously maximizing the humanization of the antibody.

The amino acid sequence of a representative heavy chain variable region derived from murine monoclonal antibody CLB-8 and a human antibody are shown in Example 2 below.

The amino acid sequence of a representative chimeric light chain variable region derived from murine monoclonal antibody CLB-8 and a human antibody is also shown in Example 2.

A chimeric antibody containing variable regions from the murine CLB-8 antibody has been demonstrated in accordance with the present invention to be as effective as murine monoclonal antibody CLB-8 in binding to IL-6.

Methods for engineering or humanizing non-human or human antibodies can also be used and are well known in the art. Generally, a humanized or engineered antibody has one or more amino acid residues from a source which is non-human, e.g., but not limited to mouse, rat, rabbit, non-human primate or other mammal. These human amino acid residues are often referred to as "import" residues, which are typically taken from an "import" variable, constant or other domain of a known human sequence. Known human Ig sequences are disclosed, e.g., in a number of public databases such as the NCBI database of the National Institute of Health or publications such as Kabat et al., Sequences of Proteins of Immunological Interest, U.S. Dept. Health (1983).

Such imported sequences can be used to reduce immunogenicity or reduce, enhance or modify binding, affinity, on-rate, off-rate, avidity, specificity, half-life, or any other suitable characteristic, as known in the art. Generally part or all of the non-human or human CDR sequences are maintained while the non-human sequences of the variable and constant regions are replaced with human or other amino acids. Antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein The human constant region of the chimeric antibody of the invention can be of any class (IgG, IgA, IgM, IgE, IgD, etc.) or isotype and can comprise a kappa or lambda light chain. In one embodiment, the human constant region comprises an IgG heavy chain or defined fragment, for example, at least one of isotypes, IgG1, IgG2, IgG3 or IgG4. In another embodiment, the anti-human IL-6 human antibody comprises an IgG1 heavy chain and a IgG1 K light chain. The isolated anti-IL-6 antibodies of the present invention comprise antibody amino acid sequences disclosed herein encoded by any suitable polynucleotide as well as. Preferably, the antibody or antigen-binding fragment binds human IL-6 and, thereby partially or substantially neutralizes at least one biological activity of the protein. The cCLB-8 antibody, or specified portion or variant thereof, partially or preferably substantially neutralizes at least one biological activity of at least one IL-6 protein or fragment and thereby inhibit activities mediated through the binding of IL-6 to the IL-6 receptor or through other IL-6-dependent or mediated mechanisms. As used herein, the term "neutralizing antibody" refers to an antibody that can inhibit an IL-6-dependent activity by about 20–120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-IL-6 antibody to inhibit an IL-6-dependent activity is preferably assessed by at least one suitable IL-6 protein or receptor assay, as described herein and/or as known in the art.

At least one antibody of the invention binds at least one specified epitope specific to at least one IL-6 protein, subunit, fragment, portion or any combination thereof to which the CLB-8 antibody binds. The at least one epitope can comprise at least one antibody binding region that comprises at least one portion of the protein, which epitope is preferably comprised of at least one extracellular, soluble, hydrophillic, external or cytoplasmic portion of the protein. Generally, the human antibody or antigen-binding fragment of the present invention will comprise an antigen-binding region that comprises at least one human complementarity determining region (CDR 1, CDR2 and CDR3) of SEQ ID NOS. 1, 2 and 3 or variant of at least one heavy chain variable region and at least one human complementarity determining region (CDR4, CDR5 and CDR6) (SEQ ID NO. 4, 5 and 6) or variant of at least one light chain variable region. As a non-limiting example, the antibody or antigen-binding portion or variant can comprise at least one of the heavy chain CDR3 having the amino acid sequence of SEQ ID NO:3, and/or a light chain CDR3 having the amino acid sequence of SEQ ID NO:6. In a particular embodiment, the antibody or antigen-binding fragment can have an antigen-binding region that comprises at least a portion of at least one heavy chain CDR (i.e., CDR1, CDR2 and/or CDR3) having the amino acid sequence of the corresponding CDRs 1, 2 and/or 3 (e.g., SEQ ID NOS:1, 2, and/or 3). In another particular embodiment, the antibody or antigen-binding portion or variant can have an antigen-binding region that comprises at least a portion of at least one light chain CDR (i.e., CDR4, CDR5 and/or CDR6) having the amino acid sequence of the corresponding CDRs 4, 5 and/or 6 (e.g., SEQ ID NOS: 4, 5, and/or 6). In a preferred embodiment the three heavy chain CDRs and the three light chain CDRs of the antibody or antigen-binding fragment have the amino acid sequence of the corresponding CDR of at least one of mAb cCLB8, Chimeric anti-IL-6 Mab, as described herein. Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method and using any of the possible redundant codons that will result in expression of a polypeptide of the invention, for example, SEQ ID NO: 15 or 16.

Antibodies that bind to human IL-6 and that comprise the defined heavy or light chain variable region or CDR regions can be prepared using suitable methods, such as phage display (Katsube, Y., et al., *Int J. Mol. Med*, 1(5):863–868 (1998)) or methods that employ transgenic animals, as known in the art and/or as described herein. For example, the antibody, specified portion or variant can be expressed using the encoding nucleic acid or portion thereof in a suitable host cell.

As stated, the invention also relates to antibodies, antigen-binding fragments, immunoglobulin chains and CDRs comprising amino acids in a sequence that is substantially the same as an amino acid sequence described herein. Such anti-IL-6 antibodies can include one or more amino acid substitutions, delations or additions, either from natural mutations or human manipulation, as specified herein. Preferably, such antibodies or antigen-binding fragments and antibodies comprising such chains or CDRs can bind human IL-6 with high affinity (e.g., $K_D$ less than or equal to about $10^{-9}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g. charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Of course, the number of amino acid substitutions a skilled artisan would make depends on many factors, including those described above. Generally speaking, the number of amino acid substitutions, insertions or deletions for any given anti-IL-6 antibody, fragment or variant will not be more than 40, 30, 20, 19, 18, 17, 16, 15, 14, 13, 12, 11, 10, 9, 8, 7, 6, 5, 4, 3, 2, 1, such as 1–30 or any range or value therein, as specified herein.

Amino acids in an anti-IL-6 antibody of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081–1085 (1989)). The latter procedure introduces single alanine mutations at every residue in the molecule. The resulting mutant molecules are then tested for biological activity, such as, but not limited to at least one IL-6 neutralizing activity. Sites that are critical for antibody binding can also be identified by structural analysis such as crystallization, nuclear magnetic resonance or photoaffinity labeling (Smith, et al., J. Mol. Biol. 224:899–904 (1992) and de Vos, et al., Science 255:306–312 (1992)).

Anti-IL-6 antibodies of the present invention can include, but are not limited to, at least one portion, sequence or combination selected from 5 to all of the contiguous amino acids of at least one of SEQ ID NOS:1, 2, 3, 4, 5, 6.

A(n) anti-IL-6 antibody can further optionally comprise a polypeptide of at least one of 70–100% of the contiguous amino acids of at least one of SEQ ID NOS:7, 8.

In one embodiment, the amino acid sequence of an immunoglobulin chain, or portion thereof (e.g., variable region, CDR) has about 70–100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of the corresponding chain of at least one of SEQ ID NOS:7, 8. For example, the amino acid sequence of a light chain variable region can be compared with the sequence of SEQ ID NO:8, or the amino acid sequence of a heavy chain CDR3 can be compared with SEQ ID NO:7. Preferably, 70–100% amino acid identity (i.e., 90, 91, 92, 93, 94, 95, 96, 97, 98, 99, 100 or any range or value therein) is determined using a suitable computer algorithm, as known in the art.

Exemplary heavy chain and light chain variable regions sequences are provided in SEQ ID NOS: 7, 8. The antibodies of the present invention, or specified variants thereof, can comprise any number of contiguous amino acid residues from an antibody of the present invention, wherein that number is selected from the group of integers consisting of from 10–100% of the number of contiguous residues in an anti-IL-6 antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active antibody of the present invention. Biologically active antibodies have a specific activity at least 20%, 30%, or 40%, and preferably at least 50%, 60%, or 70%, and most preferably at least 80%, 90%, or 95%–1000% of that of the native (non-synthetic), endogenous or related and known antibody. Methods of assaying and quantifying measures of enzymatic activity and substrate specificity, are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-Δ9-octadecanoate ($C_{18}$, oleate), all cis-Δ5,8,11,14-eicosatetraenoate ($C_{20}$, arachidonate), octanedioic acid, tetradecanedioic acid, octadecanedioic acid, docosanedioic acid, and the like. Suitable fatty acid esters include monoesters of dicarboxylic acids that comprise a linear or branched lower alkyl group. The lower alkyl group can comprise from one to about twelve, preferably one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, Calif. (1996)). An activating group can be bonded directly to the organic group (e.g., hydrophilic polymer, fatty acid, fatty acid ester), or through a linker moiety, for example a divalent $C_1$–$C_{12}$ group wherein one or more carbon atoms can be replaced by a heteroatom such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., *Bioconjugate Chem.*, 3:147–153 (1992); Werlen et al., *Bioconjugate Chem.*, 5:411–417 (1994); Kumaran et al., *Protein Sci.* 6(10):2233–2241 (1997); Itoh et al., *Bioorg. Chem.*, 24(1): 59–68 (1996); Capellas et al., *Biotechnol. Bioeng.*, 56(4): 456–463 (1997)), and the methods described in Hermanson, G. T., *Bioconjugate Techniques*, Academic Press: San Diego, Calif. (1996).

The antibodies of the invention can bind human IL-6 with a wide range of affinities ($K_D$). In a preferred embodiment, at least one human mAb of the present invention can optionally bind human IL-6 with high affinity. For example, a mAb can bind human IL-6 with a $K_D$ equal to or less than about $10^{-7}$ M, such as but not limited to, 0.1–9.9 (or any range or value therein)×$10^{-7}$, $10^{-8}$, $10^{-9}$, $10^{-10}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In *Fundamental Immunology*, Paul, W. E., Ed., Raven Press: New York, N.Y. (1984); Kuby, *Janis Immunology*, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

Anti-IL-6 cCLB-8 antibodies useful in the methods and compositions of the present invention are characterized by high affinity binding to IL-6 and optionally and preferably having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (less than about 300, preferably less than about 100 measured with a double antigen enzyme immunoassay) (Elliott et al., *Lancet* 344:1125–1127 (1994), entirely incorporated herein by reference).

When cCLB8 is compared to other IL-6-specific antibodies CLB.IL-6/14 and CLB.IL-6/16, one can see the distinct characteristics of antibody affinity and epitope specificity. cCLB8, an antibody that binds IL-6 and normally blocks the interaction between IL-6 and its receptor, can inhibit nearly 100% of IL-6 function as as illustrated in both the IL-6 dependent 7TD1 cell proliferation bioassay and the IL-6 binding to IL-6 receptor Luminex based assay. In contrast, CLB.IL-6/16, an antibody that binds IL-6, but neutralizes by sterically hindering the interaction between the IL-6/IL-6R complex and the gp130 signaling component, can inhibit only 62% of the bound biotin-IL-6. Finally, an antibody that binds IL-6 but does not interfere with its biological activity, as in CLB.IL-6/14, displays no inhibition of biotin-IL-6 binding the solid phase sIL-6R/gp80.

Bispecific, heterospecific, heteroconjugate or similar antibodies can also be used that are monoclonal, humanized, antibodies that have binding specificities for at least two different antigens. In the present case, one of the binding specificities is for at least one IL-6 protein, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986), each entirely incorporated herein by reference.

Nucleic Acid Molecules

Using the information provided herein, such as the nucleotide sequences encoding at least 70–100% of the contiguous amino acids of at least one of SEQ ID NOS:1, 2, 3, 4, 5, 6, 7, 8, specified fragments, variants or consensus sequences thereof, or a deposited vector comprising at least one of these sequences, a nucleic acid molecule of the present invention encoding at least one cCLB-8 anti-IL-6 antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally with one or more introns, e.g., but not limited to, at least one specified portion of at least one CDR, as CDR1, CDR2 and/or CDR3 of at least one heavy chain (e.g., SEQ ID NOS:1–3) or light chain (e.g., SEQ ID NOS: 4–6); nucleic acid molecules comprising the coding sequence for an anti-IL-6 antibody or variable region (e.g., SEQ ID NOS:15 or 16); and nucleic acid molecules which comprise a nucleotide sequence substantially different from those described above but which, due to the degeneracy of the genetic code, still encode at least one anti-IL-6 antibody as described herein and/or as known in the art. Of course, the genetic code is well known in the art. Thus, it would be routine for one skilled in the art to generate such degenerate nucleic acid variants that code for specific anti-IL-6 antibodies of the present invention. See, e.g., Ausubel, et al., supra, and such nucleic acid variants are included in the present invention. Non-limiting examples of isolated nucleic acid molecules of the present invention include SEQ ID NOS: 9–16; corresponding to non-limiting examples of a nucleic acid encoding, respectively, HC CDR1, HC CDR2, HC CDR3, LC CDR1, LC CDR2, LC CDR3, HC variable region and LC variable region.

As indicated herein, nucleic acid molecules of the present invention which comprise a nucleic acid encoding an anti-IL-6 antibody can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides which Selectively Hybridize to a Polynucleotide as Described Herein The present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. See, e.g., Ausubel, supra; Colligan, supra, each entirely incorporated herein by reference.

Construction of Nucleic Acids

The isolated nucleic acids of the present invention can be made using (a) recombinant methods, (b) synthetic techniques, (c) purification techniques, or combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

Recombinant Methods for Constructing Nucleic Acids

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra)

Nucleic Acid Screening and Isolation Methods

A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70–100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; U.S. Pat. Nos. 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses antisense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention further provides recombinant expression cassettes comprising a nucleic acid of the present invention. A nucleic acid sequence of the present invention, for example a cDNA or a genomic sequence encoding an antibody of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in intron) of a non-heterologous form of a polynucleotide of the present invention so as to up or down regulate expression of a polynucleotide of the present invention. For example, endogenous promoters can be altered in vivo or in vitro by mutation, deletion and/or substitution.

Vectors and Host Cells

The present invention also relates to vectors that include isolated nucleic acid molecules of the present invention, host cells that are genetically engineered with the recombinant vectors, and the production of at least one anti-IL-6 antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in E. coli and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1–4 and 16–18; Ausubel, supra, Chapters 1, 9, 13, 15, 16.

At least one antibody of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29–17.42 and 18.1–18.74; Ausubel, supra, Chapters 16, 17 and 18.

Those of ordinary skill in the art are knowledgeable in the numerous expression systems available for expression of a nucleic acid encoding a protein of the present invention.

Alternatively, nucleic acids of the present invention can be expressed in a host cell by turning on (by manipulation) in a host cell that contains endogenous DNA encoding an antibody of the present invention. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (world wide web.atcc.org). Preferred host cells include cells of lymphoid origin such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773–781 (1983)). Additionally, gene sequences to control replication in the host cell can be incorporated into the vector, as known in the art.

Production of an Antibody

At least one anti-IL-6 antibody of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987–2001); Sambrook, et al., Molecular Cloning: A Laboratory Manual, $2^{nd}$ Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994–2001); Colligan et al., Current Protocols in Protein Science, John Wiley & Sons, NY, N.Y., (1997–2001), each entirely incorporated herein by reference.

In one approach, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMAIWA, NEURO 2A, or the like, or heteromylomas, fusion products thereof, or any cell or fusion cell derived therefrom, or any other suitable cell line as known in the art. See, e.g., world wide web.atcc.org, world wide web.lifetech.com., and the like, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Antibodies of the present invention can also be prepared using at least one anti-IL-6 antibody encoding nucleic acid to provide transgenic animals or mammals, such as goats, cows, horses, sheep, and the like, that produce such antibodies in their milk. Such animals can be provided using known methods. See, e.g., but not limited to, U.S. Pat. Nos. 5,827,690; 5,849,992; 4,873,316; 5,849,992; 5,994,616, 5,565,362; 5,304,489, and the like, each of which is entirely incorporated herein by reference.

Antibodies of the present invention can additionally be prepared using at least one anti-IL-6 antibody encoding nucleic acid to provide transgenic plants and cultured plant cells (e.g., but not limited to tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95–118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127–147 (1999) and references cited therein. antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101–109 (1998) and reference cited therein. Thus, antibodies of the present invention can also be produced using transgenic plants, according to know methods. See also, e.g., Fischer et al., Biotechnol. Appl. Biochem. 30:99–108 (October, 1999), Ma et al., Trends Biotechnol. 13:522–7 (1995); Ma et al., Plant Physiol. 109:341–6 (1995); Whitelam et al., Biochem. Soc. Trans. 22:940–944 (1994); and references cited therein. See, also generally for plant expression of antibodies, but not limited to, Each of the above references is entirely incorporated herein by reference.

Purification of an Antibody

An anti-IL-6 antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997–2001), e.g., Chapters 1, 4, 6, 8, 9, 10, each entirely incorporated herein by reference.

Antibodies of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated, with glycosylated preferred. Such methods are described in many standard laboratory manuals, such as Sambrook, supra, Sections 17.37–17.42; Ausubel, supra, Chapters 10, 12, 13, 16, 18 and 20, Colligan, Protein Science, supra, Chapters 12–14, all entirely incorporated herein by reference.

Cloning and Expression of IL-6 Antibody in Mammalian Cells

A typical mammalian expression vector contains at least one promoter element, which mediates the initiation of transcription of mRNA, the antibody coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pIRES1neo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded antibody. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227:277–279 (1991); Bebbington, et al., Bio/Technology 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of antibodies.

The expression vectors pC1 and pC4 contain the strong promoter (LTR) of the Rous Sarcoma Virus (Cullen, et al., Molec. Cell. Biol. 5:438–447 (1985)) plus a fragment of the CMV-enhancer (Boshart, et al., Cell 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Cloning and Expression in CHO Cells

The vector pC4 is used for the expression of IL-6 antibody. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (e.g., alpha minus MEM, Life Technologies, Gaithersburg, Md.) supplemented with the chemotherapeutic agent methotrexate. The amplification of the DHFR genes in cells resistant to methotrexate (MTX) has been well documented (see, e.g., F. W. Alt, et al., J. Biol. Chem. 253:1357–1370 (1978); J. L. Hamlin and C. Ma, Biochem. et Biophys. Acta 1097:107–143 (1990); and M. J. Page and M. A. Sydenham, Biotechnology 9:64–68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and overexpressed. It is known in the art that this approach can be used to develop cell lines carrying more than 1,000 copies of the amplified gene(s). Subsequently, when the methotrexate is withdrawn, cell lines are obtained that contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., Molec. Cell. Biol. 5:438–447 (1985)) plus a fragment isolated from the enhancer of the immediate early gene of human cytomegalovirus (CMV) (Boshart, et al., Cell 41:521–530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human b-actin promoter, the SV40 early or late promoters or the long terminal repeats from other retroviruses, e.g., HIV and HTLVI. Clontech's Tet-Off and Tet-On gene expression systems and similar systems can be used to express the IL-6 in a regulated way in mammalian cells (M. Gossen, and H. Bujard, Proc. Natl. Acad. Sci. USA 89: 5547–5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with restriction enzymes and then dephosphorylated using calf intestinal phosphatase by procedures known in the art. The vector is then isolated from a 1% agarose gel.

The DNA sequence encoding the complete IL-6 antibody is used, e.g., as presented in SEQ ID NOS: 7, and 8, corresponding to HC and LC variable regions of a IL-6 antibody of the present invention, according to known method steps. Isolated nucleic acid encoding a suitable human constant region (i.e., HC and LC regions) is also used in this construct.

The isolated variable and constant region encoding DNA and the dephosphorylated vector are then ligated with T4 DNA ligase. E. coli HB101 or XL-1 Blue cells are then transformed and bacteria are identified that contain the fragment inserted into plasmid pC4 using, for instance, restriction enzyme analysis.

Chinese hamster ovary (CHO) cells lacking an active DHFR gene are used for transfection. 5 μg of the expression plasmid pC4 is cotransfected with 0.5 μg of the plasmid pSV2-neo using lipofectin. The plasmid pSV2neo contains a dominant selectable marker, the neo gene from Tn5 encoding an enzyme that confers resistance to a group of antibiotics including G418. The cells are seeded in alpha minus MEM supplemented with 1 μg/ml G418. After 2 days, the cells are trypsinized and seeded in hybridoma cloning plates (Greiner, Germany) in alpha minus MEM supplemented with 10, 25, or 50 ng/ml of methotrexate plus 1 μg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 mM, 2 mM, 5 mM, 10 mM, 20 mM). The same procedure is repeated until clones are obtained that grow at a concentration of 100–200 mM. Expression of the desired gene product is analyzed, for instance, by SDS-PAGE and Western blot or by reverse phase HPLC analysis.

Anti-Idiotype Antibodies to Anti-Il-6 Antibody Composition

In addition to monoclonal or chimeric anti-IL-6 antibodies, the present invention is also directed to an anti-idiotypic (anti-Id) antibody specific for such antibodies of the invention. An anti-Id antibody is an antibody which recognizes unique determinants generally associated with the antigen-binding region of another antibody. The anti-Id can be prepared by immunizing an animal of the same species and genetic type (e.g. mouse strain) as the source of the Id antibody with the antibody or a CDR containing region thereof. The immunized animal will recognize and respond to the idiotypic determinants of the immunizing antibody and produce an anti-Id antibody. The anti-Id antibody may also be used as an "immunogen" to induce an immune response in yet another animal, producing a so-called anti-anti-Id antibody.

Anti-Il-6 Antibody Compositions

The present invention also provides at least one anti-IL-6 antibody composition comprising at least one, at least two, at least three, at least four, at least five, at least six or more anti-IL-6 antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the anti-IL-6 antibody amino acid sequence selected from the group consisting of 70–100% of the contiguous amino acids of SEQ ID NOS:1, 2, 3, 4, 5, 6, 7, 8, or specified fragments, domains or variants thereof. Preferred anti-IL-6 antibody compositions include at least one or two full length, fragments, domains or variants as at least one CDR or LBR containing portions of the anti-IL-6 antibody sequence of 70–100% of SEQ ID NOS:1, 2, 3, 4, 5, 6, or specified fragments, domains or variants thereof. Further preferred compositions comprise 40–99% of at least one of 70–100% of SEQ ID NOS:1, 2, 3, 4, 5, 6, or specified fragments, domains or variants thereof. Such composition percentages are by weight, volume, concentration, molarity, or molality as liquid or dry solutions, mixtures, suspension, emulsions or colloids, as known in the art or as described herein.

Anti-IL-6 antibody compositions of the present invention can further comprise at least one of any suitable and effective amount of a composition or pharmaceutical composition comprising at least one anti-IL-6 antibody to a cell, tissue, organ, animal or patient in need of such modulation, treatment or therapy, optionally further comprising at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Non-limiting examples of such cytokines include, but are not limted to, any of IL-1 to IL-23. Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Such anti-cancer or anti-infectives can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), Staphylococcal enterotoxin A (SEA), B (SEB), or C (SEC), Streptococcal enterotoxins and the like. Such bacteria include, but are not limited to, strains of a species of enterotoxigenic *E. coli* (ETEC), enterohemorrhagic *E. coli* (e.g., strains of serotype 0157: H7), *Staphylococcus* species (e.g., *Staphylococcus aureus, Staphylococcus pyogenes*), *Shigella* species (e.g., *Shigella dysenteriae, Shigella flexneri, Shigella boydii,* and *Shigella sonnei*), *Salmonella* species (e.g., *Salmonella typhi, Salmonella cholera-suis, Salmonella enteritidis*), *Clostridium* species (e.g., *Clostridium perfringens, Clostridium dificile, Clostridium botulinum*), *Camphlobacter* species (e.g., *Camphlobacter jejuni, Camphlobacter fetus*), *Heliobacter* species, (e.g., *Heliobacter pylon*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios cholerae, Vibrios parahemolyticus*), *Klebsiella* species, *Pseudomonas aeruginosa,* and *Streptococci.* See, e.g., Stein, ed., INTERNAL MEDICINE, 3rd ed., pp 1–13, Little, Brown and Co., Boston, (1990); Evans et al., eds., Bacterial Infections of Humans: Epidemiology and Control, 2d. Ed., pp 239–254, Plenum Medical Book Co., New York (1991); Mandell et al, Principles and Practice of Infectious Diseases, 3d. Ed., Churchill Livingstone, N.Y. (1990); Berkow et al, eds., *The Merck Manual,* 16th edition, Merck and Co., Rahway, N.J., 1992; Wood et al, FEMS Microbiology Immunology, 76:121–134 (1991); Marrack et al, Science, 248:705–711 (1990), the contents of which references are incorporated entirely herein by reference.

Anti-IL-6 antibody compounds, compositions or combinations of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., *Remington's Pharmaceutical Sciences,* $18^{th}$ Edition, Mack Publishing Co. (Easton, Pa.) 1990. Pharmaceutically acceptable carriers can be routinely selected that are suitable for the mode of administration, solubility and/or stability of the anti-IL-6 antibody, fragment or variant composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1–99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-IL-6 antibody compositions can also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts such as citrate.

Additionally, anti-IL-6 antibody compositions of the invention can include polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the anti-IL-6 antibody, portion or variant compositions according to the invention are known in the art, e.g., as listed in "Remington: The Science & Practice of Pharmacy", 19$^{th}$ ed., Williams & Williams, (1995), and in the "Physician's Desk Reference", 52$^{nd}$ ed., Medical Economics, Montvale, N.J. (1998), the disclosures of which are entirely incorporated herein by reference. Preferrred carrier or excipient materials are carbohydrates (e.g., saccharides and alditols) and buffers (e.g., citrate) or polymeric agents.

Formulations

As noted above, the invention provides for stable formulations, which is preferably a phosphate buffer with saline or a chosen salt, as well as preserved solutions and formulations containing a preservative as well as multi-use preserved formulations suitable for pharmaceutical or veterinary use, comprising at least one anti-IL-6 antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001–5%, or any range or value therein, such as, but not limited to 0.001, 0.003, 0.005, 0.009, 0.01, 0.02, 0.03, 0.05, 0.09, 0.1, 0.2, 0.3, 0.4., 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1–2% m-cresol (e.g., 0.2, 0.3. 0.4, 0.5, 0.9, 1.0%), 0.1–3% benzyl alcohol (e.g., 0.5, 0.9, 1.1., 1.5, 1.9, 2.0, 2.5%), 0.001–0.5% thimerosal (e.g., 0.005, 0.01), 0.001–2.0% phenol (e.g., 0.05, 0.25, 0.28, 0.5, 0.9, 1.0%), 0.0005–1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one anti-IL-6 antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one anti-IL-6 antibody, and a second vial comprising an aqueous diluent of prescribed buffer or preservative, wherein said packaging material comprises a label that instructs a patient to reconstitute the at least one anti-IL-6 antibody in the aqueous diluent to form a solution that can be held over a period of twenty-four hours or greater.

The at least one anti-IL-6 antibody used in accordance with the present invention can be produced by recombinant means, including from mammalian cell or transgenic preparations, or can be purified from other biological sources, as described herein or as known in the art.

The range of at least one anti-IL-6 antibody in the product of the present invention includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8. Preferred buffers include phosphate buffers, most preferably sodium phosphate, particularly phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block co-polymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one anti-IL-6 antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-IL-6 antibody and preservative in an aqueous diluent is carried out using conventional dissolution and mixing procedures. To prepare a suitable formulation, for example, a measured amount of at least one anti-IL-6 antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed formulations can be provided to patients as clear solutions or as dual vials comprising a vial of lyophilized at least one anti-IL-6 antibody that is reconstituted with a second vial containing water, a preservative and/or excipients, preferably a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period of immediately to twenty-four hours or greater. Accordingly, the presently claimed articles of manufacture offer significant advantages to the patient. Formulations of the invention can optionally be safely stored at temperatures of from about 2 to about 40° C. and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to 1–12 months, one-half, one and a half, and/or two years.

The solutions of at least one anti-IL-6 antibody in the invention can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and optionally a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one anti-IL-6 antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one anti-IL-6 antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising these single vial systems include those pen-injector devices for delivery of a solution such as BD Pens, BD Autojector®, Humaject®, NovoPen®, B-D® Pen, AutoPen®, and OptiPen®, GenotropinPen®, Genotronorm Pen®, Humatro Pen®, Reco-Pen®, Roferon Pen®, Biojector®, iject®, J-tip Needle-Free Injector®, Intraject®, Medi-Ject®, e.g., as made or developed by Becton Dickensen (Franklin Lakes, N.J., world wide web.bectondickenson.com), Disetronic (Burgdorf, Switzerland, world wide web. disetronic.com; Bioject, Portland, Oreg. (world wide web.bioject.com); National Medical Products, Weston Medical (Peterborough, UK, world wide web.weston-medical.com), Medi-Ject Corp (Minneapolis, Minn., world wide web.mediject.com). Recognized devices comprising a dual vial system include those pen-injector systems for reconstituting a lyophilized drug in a cartridge for delivery of the reconstituted solution such as the HumatroPen®.

The products presently claimed include packaging material. The packaging material provides, in addition to the information required by the regulatory agencies, the conditions under which the product can be used. The packaging material of the present invention provides instructions to the patient to reconstitute the at least one anti-IL-6 antibody in the aqueous diluent to form a solution and to use the solution over a period of 2–24 hours or greater for the two vial, wet/dry, product. For the single vial, solution product, the label indicates that such solution can be used over a period of 2–24 hours or greater. The presently claimed products are useful for human pharmaceutical product use.

The formulations of the present invention can be prepared by a process that comprises mixing at least one anti-IL-6 antibody and a selected buffer, preferably a phosphate buffer containing saline or a chosen salt. Mixing the at least one antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized at least one anti-IL-6 antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

At least one anti-IL-6 antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications

IL-6, due to its pleiotropic activity, is implicated in the pathology of a variety of diseases. Therefore, a high affinity, neutralizing chimeric or human antibody to IL-6 would be desirable to be used in IL-6 related diseases such as cancer, cachexia, SLE, rheumatoid arthiritis, osteoporosis, brain trauma, cerebral edema, depression, and CHF. cCLB8 or any derivatives of this mAb including chimeric or humanized, or fragments can be used in alleviating bone pain, inhibiting growth of tumors such as melanoma, renal, prostate, breast, lung, colon cancer and multiple myeloma, lymphoproliferative disorders and other diseases in which IL-6 has been implicated. This antibody can be used either as a single agent or in combination with other therapeutic agents. In addition, this Mab can be used as a chemosensitizer whereby it can increase therapeutic efficacy of cytotoxic agents. This antibody can be used as a radiosensitizer whereby it can improve efficacy of radiation. It can also be used in combination with other tumor-immunomodulating agents such as IL-2, IL-12 and/or IFNalpha.

Thus, the present invention also provides a method for modulating or treating at least one IL-6 related disease, in a cell, tissue, organ, animal, or patient, as known in the art or as described herein, using at least one anti-IL-6 antibody of the present invention.

IL-6 is known to enhance proliferation, differentiation and survival of malignant plasma cells in multiple myeloma (MM) through an autocrine or a paracrine mechanism that involves the inhibition of apoptosis of the malignant cells. MM is an incurable malignant plasma cell disorder where, blocking IL-6 has been postulated to be an effective therapy (Anderson et al., Multiple Myeloma: New Insights and Therapeutic Approaches. Hematology: 147–165, 2000). IL-6 also has a tumorigenic effect in basal cell carcinoma where IL-6 transfected cells showed increased tumor growth rate by both suppressing apoptosis and actively promoting (Jee et al., Overexpression of interleukin-6 in human basal cell carcinoma cell lines increases anti-apoptotic activity and tumorigenic potency. Oncogene, Vol. 20, No. 2 pp. 198–208, 2001). IL-6 can also promote resistance of breast cancer cells to chemotherapy by inducing mdr1 gene expression (mdr1 and metallothionein pathways) (Conze et al, Autocrine Production of Interleukin 6 Causes Multidrug Resistance in Breast Cancer Cells. Cancer Res 61: 8851–8858, 2001).

The ability of IL-6 to mediate tumor cell survival and disease progression was confirmed by the inhibitory effects of an anti-IL-6 mAb on tumor growth both in vitro and in vivo. It was reported that blockade of IL-6 can inhibit growth of human brain tumors (glioblastoma) in vitro (Goswami et al., Interleukin-6-mediated autocrine growth promotion in human glioblastoma multiforme cell line U87MG. J Neurochem 71: 1837–1845, 1998). Using the same approach it was shown that injection of murine CLB8 anti-IL-6 antibody prolonged the survival of human tumor bearing mice (Mauray et al., Epstein-Barr virus-dependent lymphoproliferative disease: critical role of IL-6. Eur J Immunol; 30(7):2065–73, 2000). It was also reported that mCLB8 anti-IL-6 antibody regressed growth of human renal carcinoma tumors and decreased serum calcium concentrations in nude mice (Weisglass et al., The role of interleukin-6 in the induction of hypercalcemia in renal cell carcinoma transplanted into nude mice. Endocrinology 138(5):1879–8., 1995). CLB-8 antibody also regressed established human hormone refractory prostate tumor xenografts in mice (Smith et al. 2001) Anti-interleukin-6 monoclonal antibody induces regression of human prostate cancer xenografts in nude mice (Smith and Keller, Prostate; 48(1):47–53).

IL-6 can also be a prognostic factor and a marker for malignancies. In renal cell carcinoma (RCC) high levels of IL-6 were reported to correlate with tumor metastasis and eventually to poor prognosis and short survival (Jean-Yves Blay et al. 1992). Moreover, in RCC, elevated serum IL-6 is associated with poor response to IL-2 therapy (Fumagalli et al. 1999) Pretreatment serum markers and lymphocyte response to interleukin-2 therapy. Br J Cancer 80(3–4): 407–11 and correlated with the degree of IL-2 associated toxicity (Capuron et al. 2001) Association between immune activation and early depressive symptoms in cancer patients treated with interleukin-2-based therapy. Psychoneuroendocrinology; 26(8):797–808.

Elevated levels of IL-6 also correlated with poor prognosis and the presence of metastatic disease in breast cancer (Kurebayashi 2000 and Benoy 2002) Regulation of interleukin-6 secretion from breast cancer cells and its clinical implications. Breast Cancer; 7(2):124–9. Serum interleukin 6, plasma VEGF, serum VEGF, and VEGF platelet load in breast cancer patients. Clin Breast Cancer; 2(4):311–5.

IL-6 is hypothesized to be a causative factor in cancer-related morbidity such as asthenia/cachexia and bone resorption. Tumor-induced cachexia (Cahlin et al. 2000) and bone resorption (subsequent hypercalcemia) (Sandhu et al. 1999) were found to be diminished in IL-6 knockout mice. Cancer-associated depression, and cerebral edema secondary to brain tumors have also been associated with high levels of IL-6 (Musselman et al. 2001). cCLB8 antiIL-6 antibody of the invention also inhibited human melanoma and human prostate carcinoma induced cachexia in nude mice.

Clinical Experience with Anti-IL-6 Agents

Several clinical trials using monoclonal antibodies against IL-6 have been conducted in multiple diseases including plasma cell leukemia, multiple myeloma, B-lympho-proliferative disorder, rheumatoid arthritis, renal carcinoma, and AIDS associated lymphoma.

A Phase I dose escalating study with the anti-IL-6 cCLB-8 antibody of the present invention for the treatment of refractory patients with advanced stage multiple myeloma (N=12) demonstrated that some patients had disease stabilization. After discontinuation of treatment there was acceleration in the increase of M protein levels, suggesting disease re-bound after the withdrawal of therapy. Anti-IL-6 cCLB-8 antibody inhibited free circulating IL-6. Most importantly no toxicity (except transient thrombocytopenia in two heavily pretreated patients) or allergic reactions were observed. C-reactive protein (CRP) decreased below detection level in all patients. Anti-IL-6 cCLB-8 antibody demonstrated a long circulating half-life of 17.8 days, and there was no human anti-chimeric antibody (HACA) immune response observed (van Zaanen et al. 1998). Administration of CNTO 328 did not cause changes in blood pressure, pulse rate, temperature, hemoglobin, liver functions and renal functions. Except for transient thrombocytopenia in two heavily pretreated patients, no toxicity or allergic reactions were observed, and there was no human anti-chimeric antibody (HACA) immune response observed. Three patients developed infection-related complications during therapy, however, a possible relation with anti-IL-6 cCLB-8 antibody was unlikely because infectious complications are common in end stage multiple myeloma and are a major cause of death. In addition all three patients were able to respond to their infection even in the presence of anti-IL-6 cCLB-8 antibody, suggesting that anti-IL-6 therapy is not able to block IL-6 during infection. No treatment-associated fatalities were reported. In conclusion, results from this study suggest that anti-IL-6 cCLB-8 antibody was safe in multiple myeloma patients.

Thus, the present invention provides a method for modulating or treating at least one malignant disease in a cell, tissue, organ, animal or patient, including, but not limited to, at least one of: multiple myeloma, leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignamt lymphoma, non-hodgkin's lymphoma, Burkitt's lymphoma, multiple myeloma, Kaposi's sarcoma, colorectal carcinoma, renal cell carcinoma, pancreatic carcinoma, prostatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain; the suppression of cancer metastasis; the amelioration of cancer cachexia; and the treatment of inflammatory diseases such as mesangial proliferative glomerulonephritis and the like. Such a method can optionally be used in combination with, by administering before, concurrently or after administration of such IL-6 antibody, radiation therapy, an anti-angiogenic agent, a chemotherapeutic agent, a farnesyl transferase inhibitor or the like.

The present invention also provides a method for modulating or treating at least one Il-6 mediated immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondilitis, gastric ulcer, seronegative arthropathies, asteoarthritis, inflammatory bowel disease, ulverative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitivity reactions, allergic rhinitis, hay fever, perennial rhinitis, conjunctivitis, endometriosis, asthma, urticaria, systemic anaphalaxis, dermatitis, pernicious anemia, hemolytic disesease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited to asthenia, anemia, cachexia, and the like), chronic salicylate intoxication, sleep apnea, obesity, heart failure, sinusitis, inflammatory bowel disease, and the like. See, e.g., the Merck Manual, 12th–17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

The present invention also provides a method for modulating or treating at least one infectious disease in a cell, tissue, organ, animal or patient, including, but not limited to, at least one of: acute or chronic bacterial infection, acute and chronic parasitic or infectious processes, including bacterial, viral and fungal infections, HIV infection/HIV neuropathy, meningitis, hepatitis (A, B or C, or the like), septic arthritis, peritonitis, pneumonia, epiglottitis, e. coli 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, mycobacterium tuberculosis, mycobacterium avium intracellulare, pneumocystis carinii pneumonia, pelvic inflammatory disease, orchitis/epidydimitis, legionella, lyme disease, influenza a, epstein-barr virus, vital-associated hemaphagocytic syndrome, vital encephalitis/aseptic meningitis, and the like;

Any of such methods can optionally comprise administering an effective amount of at least one composition or pharmaceutical composition comprising at least one anti-IL-6 antibody to a cell, tissue, organ, animal or patient in need of such modulation, treatment or therapy. Indications for treatment with ant-IL-6 therapy are disclosed in the following references, hereby incorporated by reference into the present application: Van Snick, "Interleukin-6: An Overview," Ann. Rev. Immunol., 8:253–278 (1990); Campbell et al., "Essential Role for Interferon-gamma. And Interleukin-6 in Autoimmune Insulin-Dependent Diabetes in NOD/Wehi Mice," J. Clin. Invest., 87:739–742 (1991); Heinrich et al., "Interleukin-6 Monoclonal Antibody Therapy for a Patient with Plasma Cell Leukemia," Blood, 78(5):1198–1204 (1991); Starnes et al., "Anti-IL-6 Monoclonal Antibodies Protect Against Lethal *Escherichia coli* Infection and Lethal Tumor Necrosis Factor-alpha. Challenge in Mice," J. Immunol., 145(12):4185–4191 (1990); Strassman et al., "Evidence for the Involvement of Interleukin 6 in Experimental Cancer Cachexia," J. Clin. Invest., 89:1681–1684 (1992).

Any method of the present invention can comprise administering an effective amount of a composition or pharmaceutical composition comprising at least one anti-IL-6 antibody to a cell, tissue, organ, animal or patient in need of such modulation, treatment or therapy. Such a method can optionally further comprise co-administration or combination therapy for treating such immune diseases or malignant diseases, wherein the administering of said at least one anti-IL-6 antibody, specified portion or variant thereof, further comprises administering, before concurrently, and/or after, at least one selected from at least one TNF antagonist (e.g., but not limited to a TNF antibody or fragment, a soluble TNF receptor or fragment, fusion proteins thereof, or a small molecule TNF antagonist), an IL-18 antibody or fragment, small molecule IL-18 antagonist or IL-18 receptor binding protein, an IL-1 antibody (including both IL-1 alpha and IL-1 beta) or fragment, a soluble IL-1 receptor antagonist, an antirheumatic (e.g., methotrexate, auranofin, aurothioglucose, azathioprine, etanercept, gold sodium thiomalate, hydroxychloroquine sulfate, leflunomide, sulfasalazine, radiation therapy, an anti-angiogenic agent, a chemotherapeutic agent, Thalidomide, a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., Pharmacotherapy Handbook, 2$^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

TNF antagonists suitable for compositions, combination therapy, co-administration, devices and/or methods of the present invention (further comprising at least one anti body, specified portion and variant thereof, of the present invention), include, but are not limited to, anti-TNF antibodies, antigen-binding fragments thereof, and receptor molecules which bind specifically to TNF; compounds which prevent and/or inhibit TNF synthesis, TNF release or its action on target cells, such as thalidomide, tenidap, phosphodiesterase inhibitors (e.g, pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

Therapeutic Treatments.

Any method of the present invention can comprise a method for treating an IL-6 mediated disorder, comprising administering an effective amount of a composition or pharmaceutical composition comprising at least one anti-IL-6 antibody to a cell, tissue, organ, animal or patient in need of such modulation, treatment or therapy. Such a method can optionally further comprise co-administration or combination therapy for treating such immune diseases, wherein the administering of said at least one anti-IL-6 antibody, specified portion or variant thereof, further comprises administering, before concurrently, and/or after, at least one agent as described above.

Typically, treatment of pathologic conditions is effected by administering an effective amount or dosage of at least one anti-IL-6 antibody composition that total, on average, a range from at least about 0.01 to 500 milligrams of at least one anti-IL-6 antibody per kilogram of patient per dose, and preferably from at least about 0.1 to 100 milligrams antibody/kilogram of patient per single or multiple administration, depending upon the specific activity of contained in the composition. Alternatively, the effective serum concentration can comprise 0.1–5000 µg/ml serum concentration per single or multiple adminstration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100–500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5., 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.1 milligram to about 500 milligrams of active ingredient per unit or container. In these pharmaceutical compositions the active ingredient will ordinarily be present in an amount of about 0.5–99.999% by weight based on the total weight of the composition.

Parenteral Formulations and Administration

For parenteral administration, the antibody can be formulated as a solution, suspension, emulsion or lyophilized powder in association, or separately provided, with a pharmaceutically acceptable parenteral vehicle. Examples of such vehicles are water, saline, Ringer's solution, dextrose solution, and 1–10% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aquous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semi-synthtetic mono- or di- or tri-glycerides. Parental administration is known in the art and includes, but is not limited to, conventional means of injections, a gas pressured needleless injection device as described in U.S. Pat. No. 5,851,198, and a laser perforator device as described in U.S. Pat. No. 5,839,446 entirely incorporated herein by reference.

Alternative Delivery

The invention further relates to the administration of at least one anti-IL-6 antibody by parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal means. At least one anti-IL-6 antibody composition can be prepared for use for parenteral (subcutaneous, intramuscular or intravenous) or any other administration particularly in the form of liquid solutions or suspensions; for use in vaginal or rectal administration particularly in semisolid forms such as, but not limited to, creams and suppositories; for buccal, or sublingual administration such as, but not limited to, in the form of tablets or capsules; or intranasally such as, but not limited to, the form of powders, nasal drops or aerosols or certain agents; or transdermally such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement"; Hsieh, D. S., Eds., pp. 59–90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402) (the above publications and patents being entirely incorporated herein by reference).

Pulmonary/Nasal Administration

For pulmonary administration, preferably at least one anti-IL-6 antibody composition is delivered in a particle size effective for reaching the lower airways of the lung or sinuses. According to the invention, at least one anti-IL-6 antibody can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of antibodies are also known in the art. All such devices can use of formulations suitable for the administration for the dispensing of antibody in an aerosol. Such aerosols can be comprised of either solutions (both aqueous and non aqueous) or solid particles. Metered dose inhalers like the Ventolin® metered dose inhaler, typically use a propellent gas and require actuation during inspiration (See, e.g., WO 94/16970, WO 98/35888). Dry powder inhalers like Turbuhaler™ (Astra), Rotahaler® (Glaxo), Diskus® (Glaxo), Spiros™ inhaler (Dura), devices marketed by Inhale Therapeutics, and the Spinhaler® powder inhaler (Fisons), use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference). Nebulizers like AERx™ Aradigm, the Ultravent® nebulizer (Mallinckrodt), and the Acorn II® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention, and are not intended as limiting the scope of the invention. Preferably, a composition comprising at least one anti-IL-6 antibody is delivered by a dry powder inhaler or a sprayer. There are a several desirable features of an inhalation device for administering at least one antibody of the present invention. For example, delivery by the inhalation device is advantageously reliable, reproducible, and accurate. The inhalation device can optionally deliver small dry particles, e.g. less than about 10 µm, preferably about 1–5 µm, for good respirability.

Administration of IL-6 Antibody Compositions as a Spray

A spray including IL-6 antibody composition protein can be produced by forcing a suspension or solution of at least one anti-IL-6 antibody through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one anti-IL-6 antibody composition protein delivered by a sprayer have a particle size less than about 10 µm, preferably in the range of about 1 µm to about 5 µm, and most preferably about 2 µm to about 3 µm.

Formulations of at least one anti-IL-6 antibody composition protein suitable for use with a sprayer typically include antibody composition protein in an aqueous solution at a concentration of about 0.1 mg to about 100 mg of at least one anti-IL-6 antibody composition protein per ml of solution or mg/gm, or any range or value therein, e.g., but not limited to, 0.1, 0.2., 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/ml or mg/gm. The formulation can include agents such as an excipient, a buffer, an isotonicity agent, a preservative, a surfactant, and, preferably, zinc. The formulation can also include an excipient or agent for stabilization of the antibody composition protein, such as a buffer, a reducing agent, a bulk protein, or a carbohydrate. Bulk proteins useful in formulating antibody composition proteins include albumin, protamine, or the like. Typical carbohydrates useful in formulating antibody composition proteins include sucrose, mannitol, lactose, trehalose, glucose, or the like. The antibody composition protein formulation can also include a surfactant, which can reduce or prevent surface-induced aggregation of the antibody composition protein caused by atomization of the solution in forming an aerosol. Various conventional surfactants can be employed, such as polyoxyethylene fatty acid esters and alcohols, and polyoxyethylene sorbitol fatty acid esters. Amounts will generally range between 0.001 and 14% by weight of the formulation. Especially preferred surfactants for purposes of this invention are polyoxyethylene sorbitan monooleate, polysorbate 80, polysorbate 20, or the like. Additional agents known in the art for formulation of a protein such as IL-6 antibodies, or specified portions or variants, can also be included in the formulation.

Administration of IL-6 Antibody Compositions by a Nebulizer

Antibody composition protein can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of antibody composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of antibody composition protein either directly or through a coupling fluid, creating an aerosol including the antibody composition protein. Advantageously, particles of antibody composition protein delivered by a nebulizer have a particle size less than about 10 µm, preferably in the range of about 1 µm to about 5 µm, and most preferably about 2 µm to about 3 µm.

Formulations of at least one anti-IL-6 antibody suitable for use with a nebulizer, either jet or ultrasonic, typically include a concentration of about 0.1 mg to about 100 mg of at least one anti-IL-6 antibody protein per ml of solution. The formulation can include agents such as an excipient, a buffer, an isotonicity agent, a preservative, a surfactant, and, preferably, zinc. The formulation can also include an excipient or agent for stabilization of the at least one anti-IL-6 antibody composition protein, such as a buffer, a reducing agent, a bulk protein, or a carbohydrate. Bulk proteins useful in formulating at least one anti-IL-6 antibody composition proteins include albumin, protamine, or the like. Typical carbohydrates useful in formulating at least one anti-IL-6 antibody include sucrose, mannitol, lactose, trehalose, glucose, or the like. The at least one anti-IL-6 antibody formulation can also include a surfactant, which can reduce or prevent surface-induced aggregation of the at least one anti-IL-6 antibody caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Especially preferred surfactants for purposes of this invention are polyoxyethylene sorbitan mono-oleate, polysorbate 80, polysorbate 20, or the like. Additional agents known in the art for formulation of a protein such as antibody protein can also be included in the formulation.

Administration of IL-6 Antibody Compositions by a Metered Dose Inhaler

In a metered dose inhaler (MDI), a propellant, at least one anti-IL-6 antibody, and any excipients or other additives are contained in a canister as a mixture including a liquefied compressed gas. Actuation of the metering valve releases the mixture as an aerosol, preferably containing particles in the size range of less than about 10 µm, preferably about 1 µm to about 5 µm, and most preferably about 2 µm to about 3 µm. The desired aerosol particle size can be obtained by employing a formulation of antibody composition protein produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of at least one anti-IL-6 antibody for use with a metered-dose inhaler device will generally include a finely divided powder containing at least one anti-IL-6 antibody as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like. Preferably the propellant is a hydrofluorocarbon. The surfactant can be chosen to stabilize the at least one anti-IL-6 antibody as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. Additional agents known in the art for formulation of a protein such as protein can also be included in the formulation.

One of ordinary skill in the art will recognize that the methods of the current invention can be achieved by pulmonary administration of at least one anti-IL-6 antibody compositions via devices not described herein.

Oral Formulations and Administration

Formulations for oral administration rely on the co-administration of adjuvants (e.g., resorcinols and nonionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant such as magnesium stearate, paraben, preserving agent such as sorbic acid, ascorbic acid, .alpha.-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925,673). Furthermore, carrier compounds described in U.S. Pat. No. 5,879,681 and U.S. Pat. No. 5,5,871,753 are used to deliver biologically active agents orally are known in the art.

Mucosal Formulations and Administration

For absorption through mucosal surfaces, compositions and methods of administering at least one anti-IL-6 antibody include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g. suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include sugars, calcium stearate, magnesium stearate, pregelinatined starch, and the like (U.S. Pat. No. 5,849,695).

Transdermal Formulations and Administration

For transdermal administration, the at least one anti-IL-6 antibody is encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. No. 5,814,599).

Prolonged Administration and Formulations

It can be sometimes desirable to deliver the compounds of the present invention to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g. a zinc tannate salt. Additionally, the compounds of the present invention or, preferably, a relatively insoluble salt such as those just described, can be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above can also be formulated in cholesterol matrix silastic pellets, particularly for use in animals. Additional slow release, depot or implant formulations, e.g. gas or liquid liposomes are known in the literature (U.S. Pat. No. 5,770,222 and "Sustained and Controlled Release Drug Delivery Systems", J. R. Robinson ed., Marcel Dekker, Inc., N.Y., 1978).

Abbreviations

BSA—bovine serum albumin
EIA—enzyme immunoassay
FBS—fetal bovine serum
$H_2O_2$—hydrogen peroxide
HRP—horseradish peroxidase\
Ig—immunoglobulin
IL-6—Interleukin-6
IP—intraperitoneal
IV—intravenous
Mab—monoclonal antibody
OD—optical density OPD—o-Phenylenediamine dihydrochloride
PEG—polyethylene glycol
PSA—penicillin, streptomycin, amphotericin
RT—room temperature
SQ—subcutaneous
v/v—volume per volume
w/v—weight per volume

EXAMPLE I

Generation of Murine CLB8 MAB

Immunization

The hybridoma giving rise to the murine CLB-IL6–8 antibody was derived from a fusion performed in a laboratory of Dr. Lucien Aarden, Central Laboratory of the Netherlands Red Cross Transfusion Service (CLB) as reported (Brackenhoff et al, J. Immunol. (1990) 145: 561–568).

Eight week old female Balb/c mice obtained from CLB's specified pathogen free breeding stock were immunized intramuscularly (IM) with 10 μg of purified recombinant interleukin-6 (rIL-6) (CLB) emulsified in Complete Freund's adjuvant. Three subsequent IM injections with 10 μg each of rIL-6 in Incomplete Freund's adjuvant were carried out at intervals of 4–8 weeks.

Cell Fusion

Four days after the last IM booster injection, a mouse was sacrificed; the spleen was removed and finely minced. A single cell suspension was obtained in ambient Earle's balanced salt solution. The cells were washed and counted. A fusion was carried out at a 1:3 ratio of viable spleen cells to murine myeloma cells (SP2/0-Ag14) in the presence of 42% (w/v) polyethylene glycol in Iscove's modified Dulbecco's medium (IMDM). The non-Ig secreting fusion partner SP2/0 was established from a cell bank maintained at CLB. After fusion, cells were resuspended in IMDM, supplemented with 5% fetal bovine serum, 50 μM penicillin/streptomycin, 5×10-5 M 2-mrecaptoethanol (2-ME) and HAT (6×10-4 M hypoxanthine, 6.5×10-7 M aminopterin, 6.4×10-5 M thymidine). The proliferation of these hybridomas immediately after fusion is dependent on IL-6, therefore, 100 U/mL of purified murine IL-6 (Van Smick, Brussels) was added to the selection medium. The fused cells were then distributed into 96-well plates at 1×10$^5$ cells/100 microL well.

Primary Characterization of Murine Anti IL-6 Hybridomas

Anti-IL-6 secreting hybrids were selected by enzyme linked immunosorbent assay (ELISA) and radioimmunoassay (RIA) (Brackenhoff et al. (1990) 145: 561–568).

A solid phase ELISA was employed for screening monoclonal antibodies specific for human IL-6. Purified rIL-6 (0.5 μg/mL) was coated overnight at room temperature in phosphate buffered saline (PBS) on flat-bottomed plates (Dynatech), 100 μL/well. The plates were washed with PBS, 0.02% (v/v) Tween 20 (PBS/Tween) and were incubated with 1:2 dilutions of culture supernatants in PBS/Tween supplemented with 0.2% gelatin (PTG) for 2 hours at ambient temperature. After washing, the plates were incubated with horseradish peroxidase-conjugated monoclonal rat anti-mouse kappa light chain 226 (Einstein University, NY) in PTG (2 μg/mL) for 1 hour. The plates were washed and the bound peroxidase was detected with 100 μL/well of 3,5,3,5,tetramethylbenzidine/0.003% hydrogen peroxide in 0.1-M sodium acetate, pH 5.5. The color reaction was stopped with 2M $H_2SO_4$ and the plates were read at 450 nM on a Titertek, Multiscan reader. The wells yielding positive OD's were chosen.

A solid phase RIA was also employed for screening anti-IL-6 hybridomas. Goat anti-murine Ig antibodies were coupled to cyanogen-bromide activated sepharose CL-4B (Pharmacia). The sepharose was washed and resuspended at 10 mg/mL in PBS, 0.1% Tween 20, 0.1% sodium azide. Hybridoma supernatants were added to sepharose beads in the presence of approximately 20,000 counts/minute of $^{125}$Iodine-rIL-6 (CLB) for 6 hours with constant mixing. The beads were washed extensively in PBS/Tween and counted in a gamma counter. The wells yielding the highest specific activities were chosen.

Hybridomas that were positive in both assay systems were established and subcloned twice at limiting dilutions in IMDM supplemented with 2×10$^{-5}$ M 2-ME and 5% FBS (complete IMDM). The IL-6 independent subclone CLB-IL6–8 was selected and maintained in complete IMDM. Stock cultures tested negative for mycoplasma using an indirect Hoescht stain after 4 days in culture on Vero76 target cells. Isotype determination of supernatant via Innogenetics Line ImmunoAssay (INNO-LIA) mouse monoclonal antibody isotype kit yielded a single murine isotype IgG$_1$ kappa. This isotype determination was confirmed by a capture EIA The murine hybridoma and cell line was so produced, CLBIL-6/8 was called CLB8. It was chimerized and further characterized as described below.

EXAMPLE 2

Chimerization and Sequencing

Cloning and Expression of the cCLB8 Variable Region Genes

Genomic DNA was isolated from the murine hybridoma C143A which secretes a murine monoclonal antibody specific for human IL-6.

For the light chain, the DNA was digested with restriction endonuclease Hind m and subjected to electrophoresis through a 0.8% agarose gel. The portion of the gel containing DNA fragments approximately 3.4 Kb in length was excised, and the DNA was eluted. The fragments were ligated into the vector8charon27, and packaged into bacteriophage particles. For the heavy chain, the DNA was digested with restriction endonuclease Eco RI and subjected to electrophoresis through a 0.8% agarose gel. The portion of the gel containing DNA fragments approximately 3.6 Kb in length was excised, and the DNA was eluted. The fragments were ligated into the vector8gt10, and packaged into bacteriophage particles.

Both heavy and light chain bacteriophage libraries were plated on E. Coli, and grown overnight. The plaques were transferred to nitrocellulose filters, and probed with $^{32}$P-labeled DNA fragments corresponding to murine $J_\kappa$ (light chain) or murine $J_H$ sequences. Positive plaques were identified and plaque purified. Phage DNA was isolated, and the Hind III (light chain) or Eco RI (heavy chain) inserts were isolated and cloned into immunoglobulin expression vectors.

Heavy and light chain expression plasmids were used to cotransfect SP2/0 cells, and mycophenolic acid selection was applied. Individual clones producing chimeric antibody were identified and subcloned to insure monoclonality and to generate higher producers.

Antibody purified from individual cell lines was tested for neutralization ability in an IL-6-dependent B9 cell proliferation assay. The antibody is referred as chimeric CLB8 or cCLB8 throughout this application.

cCLB8 Heavy Chain Variable Region

```
E   V   Q   L   V   E   S   G   G   K   L   L
K   P   G   G   S   L   K   L

GAG GTG CAA CTG GTG GAA TCT GGA GGA AAA TTA CTG
AAG CCT GGA GGG TCC CTG AAA CTC

CEN 322

S   C   A   A   S   G   F   T   F   S
S   F   A   M   S   W   F   R   Q   S

TCC TGT GCA GCC TCT GGA TTC ACC TTC AGT AGC TTT
GCC ATG TCT TGG TTT CGC CAG TCT

CDR 1

P   E   K   R   L   E   W   V   A
E   I   S   S   G   G   S   Y   T   Y   Y

CCA GAG AAG AGG CTG GAG TGG GTC GCA GAA ATT AGT
AGT GGT GGG AGT TAC ACC TAC TAT

CDR 2

P   D   T   V   T   G   R   F   T   I   S   R
D   N   A   K   N   T   L   Y

CCT GAC ACT GTG ACG GGC CGA TTC ACC ATC TCC AGA
GAC AAT GCC AAG AAC ACC CTG TAC

L   E   M   S   S   L   R   S   E   D   T   A
M   Y   Y   C   A   R   G   L

CTG GAA ATG AGC AGT CTG AGG TCT GAG GAC ACG GCC
ATG TAT TAT TGT GCA AGG GGT TTA

W   G   Y   Y   A   L   D   Y   W   G   Q   G
T   S   V   T   V   S   S  SEQ ID NO: 7

TGG GGG TAC TAT GCT CTT GAC TAC TGG GGT CAA GGA
ACC TCA GTC ACC GTC TCC TCA  SEQ ID NO: 15

CDR 3
``` cCLB8 Light Chain Variable Region

```
Q   I   V   L   I   Q   S   P   A   I   M   S
A   S   P   G   E   K   V   T

CAA ATT GTT CTC ATA CAG TCT CCA GCA ATC ATG TCT
GCA TCT CCA GGG GAG AAG GTC ACC

M   T   C   S   A   S   S   S   V   S   Y   M
Y   W   Y   Q   Q   K   P   G

ATG ACC TGC AGT GCC AGC TCA AGT GTA AGT TAC ATG
TAC TGG TAC CAG CAG AAG CCA GGA
```

CEN 322

```
                                          CDR 1

S   S   P   R   L   L   I   Y
D   T   S   N   L   A   S   G   V   P   V   R

TCC TCC CCC AGA CTC CTG ATT TAT GAC ACA TCC AAC
CTG GCT TCT GGA GTC CCT GTT

CGC

CDR 2

F   S   G   S   G   S   G   T   S   Y   S   L
T   I   S   R   M   E   A   E

TTC AGT GGC AGT GGG TCT GGG ACC TCT TAC TCT CTC
ACA ATC AGC CGA ATG GAG GCT GAG

D   A   A   T   Y   Y   C
Q   Q   W   S   G   Y   P   Y   T   F   G   G
G

GAT GCT GCC ACT TAT TAC TGC CAG CAG TGG AGT GGT
TAC CCA TAC ACG TTC GGA GGG GGG

CDR 3

T   K   L   E   I   K SEQ ID NO: 8
ACC AAG CTG GAA ATA AAA  SEQ ID NO: 16
```

EXAMPLE 3

Measure of Binding of cCLB8 to Human IL-6 by Solid Phase EIA

A solid phase EIA was used to assess binding characteristics of cCLB8 Mab to human IL-6. Briefly, plates were coated with recombinant human IL-6 (RDI) at 1 μg/mL in PBS overnight at 4° C. After washing in 0.15M saline containing 0.02% (v/v) Tween 20, the wells were blocked with 1% (w/v) BSA in PBS, 200 μL/well for 1 hour at RT. Purified antibody was incubated in two-fold serial dilutions from a starting concentration of 5 μg/mL for 1 hour at 37° C. The plate was washed and then probed with 50 μL/well HRP-labeled goat anti-human IgG (Tago) diluted 1:20,000 in 1% BSA-PBS for 1 hour at RT. The plate was again washed and 100 μL/well of the citrate-phosphate substrate solution (0.1M citric acid and 0.2M sodium phosphate, 0.01% $H_2O_2$ and 1 mg/mL OPD) was added for 15 minutes at RT. Stop solution (4N sulfuric acid) was then added at 25 μL/well and the absorption at 490 nm quantitated using an automated plate photometer. FIG. 1 shows cCLB8 binding to IL-6 measured as OD 490 nm demonstrating that cCLB8 binds to recombinant human IL-6 in a concentration dependent manner.

EXAMPLE 4

In Vitro Neutralization Assays

Blockade of IL-6 by cCLB8 Inhibits Secretion of IgM and MCP-1

The chimeric monoclonal antibody cCLB8 was assessed in two simple bioassay formats to determine its neutralizing bioactivity on IL6 induced secretion of human IgM and the chemokine MCP-1. Two human cell lines were used in these studies. The SKW6.4 cell line was originally derived from an EBV transformed Burkitt's B cell lymphoma and secretes soluble IgM in response to IL6. The U937 cell line is monoblastic, committed to monocyte differentiation and was originally isolated from a patient with diffuse histiocytic lymphoma. U937 cells secrete MCP-1 in response to IL6. cCLB8 inhibition of these particular bioactivities were evaluated since they could easily be monitored using an EIA format. Prior to assay, cells were serum starved over night and then cultured the following day alone, with IL6 or with IL6 preincubated with various concentrations of antibody or a negative control antibody. At the conclusion of a 72 hour incubation supernatants were collected and used in IgM specific and MCP-1 specific EIA's. The results as shown in FIGS. 2 and 3, demonstrate cCLB8 significantly inhibits IL6 mediated secretion of IgM and MCP-1 in vitro.

Figure 2:
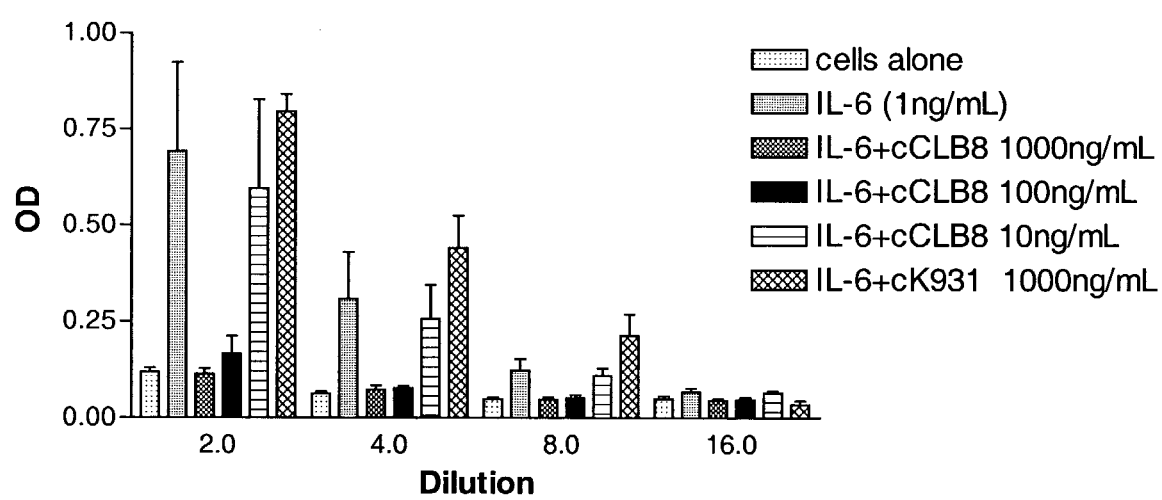
FIG. 2: Graph showing the inhibition of IL-6 mediated IgM mu secretion from SKW6.4 cells by cCLB8.

In the experiment represented by FIG. 2, EIA plates were coated with goat anti-human IgM Fc5µ fragment specific in 10 mM carbonate buffer, pH 9.6 overnight at 4° C. Plates were washed with 0.15 M saline with 0.02% v/v Tween 20 and blocked with PBS/1% w/v BSA for 1 hour. Cell culture supernatant was added at serial two-fold dilutions. Following incubation and subsequent washes with 0.02% Tween, 0.15M saline the plate was probed with HRP-labeled goat anti-human IgMµ chain specific. OPD substrate was then added and following color development, OD read at 490 nm. The data indicate that cCLB8, but not the isotype matched negative control chimeric mAb, inhibits IgM mu secretion.

Figure 3:
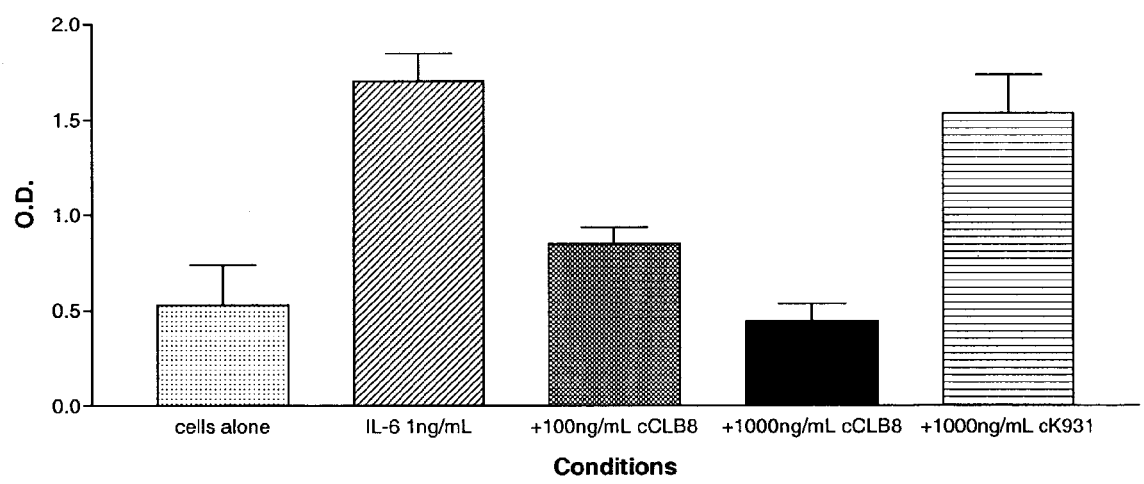
FIG. 3: Graph showing the inhibition of IL-6 mediated MCP-1 production by cCLB8.

In the experiment represented by FIG. 3, EIA plates were coated with goat anti-human MCP-1 in 10 mM carbonate buffer, pH 9.6 overnight at 4° C. Plates were washed with 0.15 M saline with 0.02% v/v Tween 20 and blocked with PBS/1% w/v BSA for 1 hour. Cell culture supernatant was added at serial two-fold dilutions. Following a two-hour incubation and subsequent washes with 0.02% Tween, 0.15M saline, the plate was probed with biotinylated anti-human MCP-1 as per manufacturer's instructions. Plates were washed again and HRP-labeled streptavidin was added for 1 hour. Color development was done with TMB substrate. OD read at 450. The data indicate that cCLB8, but not cK931, inhibit IL-6 mediated MCP-1 production.

Neutralization of IL6-Mediated Phosphorylation of STAT3.

The IL6 receptor consists of an 80 kD binding sub-unit, IL6Rα and the signal transduction sub-unit, gp130. IL6 binds to the IL6Rα sub-unit and initiates the association of IL6Rα and gp130 resulting in a high affinity receptor and signal transduction. IL6Rα also exists in a soluble form. IL6 can bind to soluble IL6R (sIL6R) and the complex can act on cells expressing gp130. IL6 has been shown to activate STAT3. A human acute monocytic leukemia cell line, THP-1, was used to demonstrate inhibition of STAT3 phosphorylation by cCLB8. Cells were stimulated with (IL6+sIL6R)+/−cCLB8 or irrelevant antibody (K931) as a negative control. Cell lysates were immunoprecipitated with anti-STAT3, samples resolved on 7.5% SDS-PAGE and transferred to Hybond-P membrane, followed by Western blotting using anti-phosphotyrosine-HRP. ECLplus was used for detection.

Figure 4:
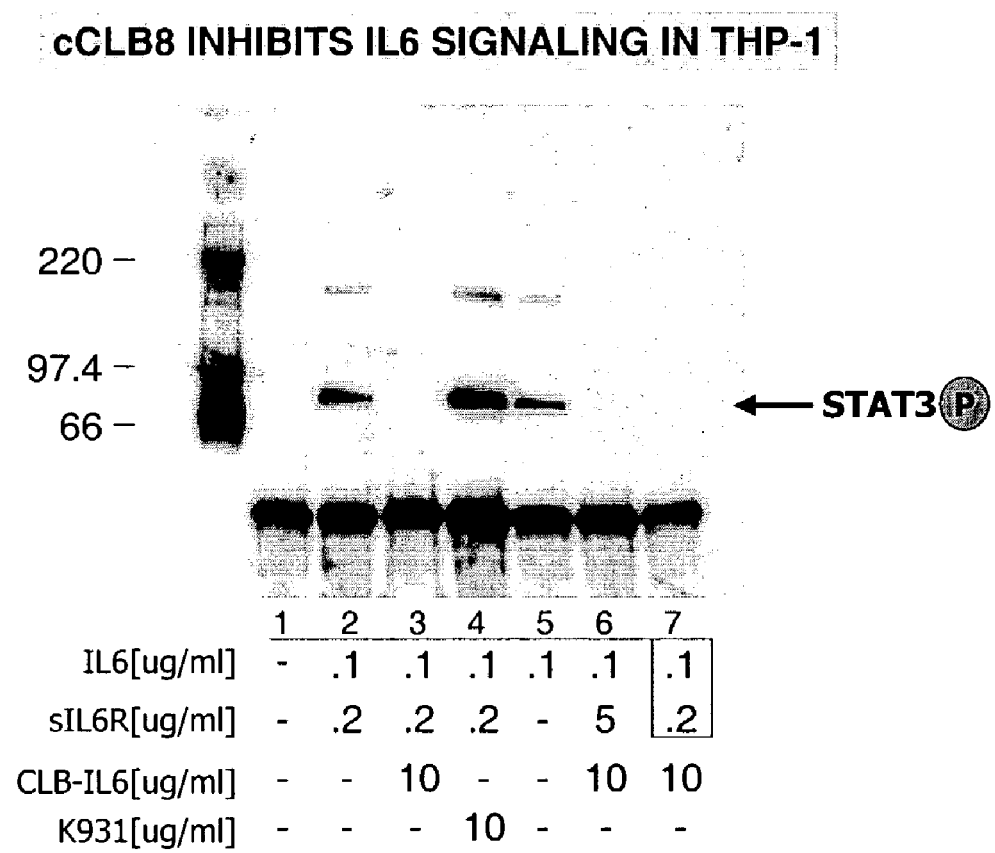
FIG. 4: Image of a western blot showing cCLB8 inhibition of IL-6 signaling in THP-1 human monocytic leukemia cells.

The data represented in FIG. 4 show that cCLB8 can inhibit phosphorylation of STAT3 when it is a) allowed to bind to rhIL6 before addition of sIL6R, b) allowed to bind to sIL6R before addition of rhIL6, or c) when rhIL6 is allowed to bind to sIL6R before addition of cCLB8 and cells. THP-1 cells incubated in media without serum for 1 hr, scraped from flasks and resuspended in 0.5 ml media Lanes 2–6, IL6 incubated +/−antibody for 15 min, then sIL6R added and incubated for 15 min. Cells added and incubated additional 15 min. Lane 7, IL6 incubated with sIL6R for 15 min, then CLB-IL6 added and incubated for 15 min. Cells added and incubated additional 15 min. Samples immunoprecipitated with anti-STAT3 [1 µg/ml], resuspended in Laemmli sample buffer and resolved on 7.5% SDS-PAGE and transferred to Hybond-P. Membrane incubated with anti-phosphotyrosine-HRP.

cCLB8 Inhibits Serum Amyloid A Production

IL-1β is a potent inducer of Serum Amyloid A (SAA) production from HepG2 human hepatoma cells in the presence of human IL-6 (Smith and McDonald, Clin Exp. Immunol. 90:293–9 (1992)). Therefore, cCLB8 Mab was assayed for the ability to inhibit IL-1β/IL-6 induced SAA production from these cells. Briefly, HepG2 cells were seeded at $2.25 \times 10^5$/well for 24 hours. IL-6 (100 ng/ml, RDI) and IL-6sR (200 ng/ml, S & D) were preincubated for 30 minutes, and mixed with IL-1β (1 ng/ml, R&D). The cCLB8 Mab and a negative isotype control Mab (cSF25) were serially diluted and then preincubated with the above mixture for 30 minutes more.

Figure 5:
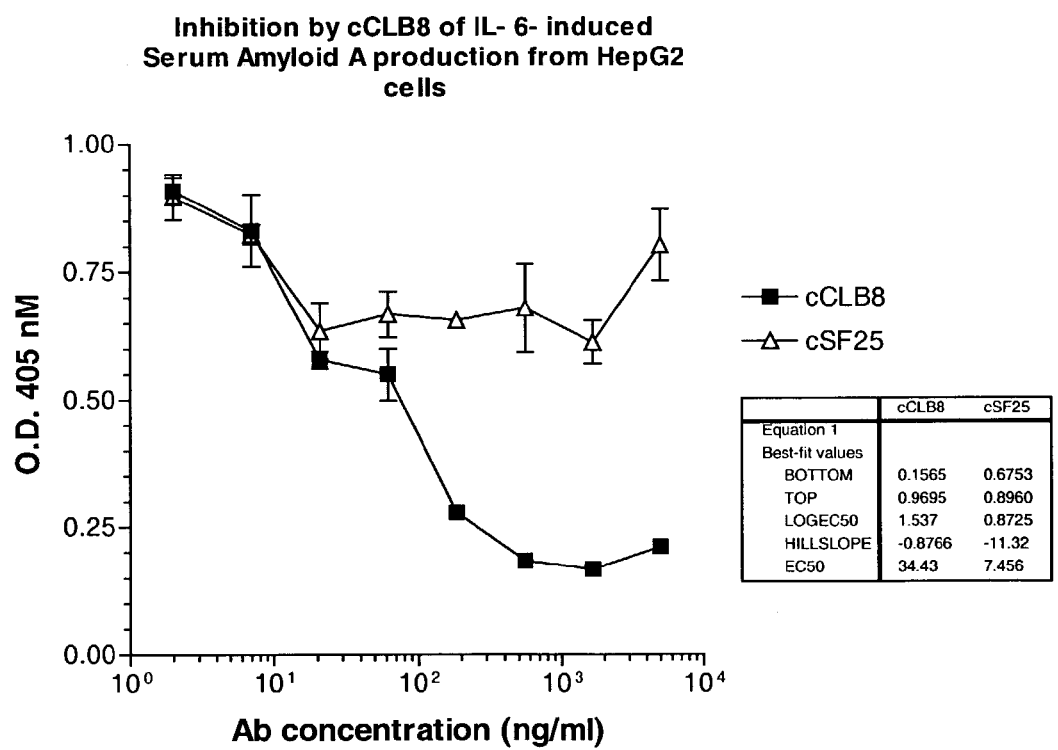
FIG. 5: Graph showing the inhibition by cCLB8 of IL-6 induced serum amyloid A production from HepG2 cells.

For the experimental results shown in FIG. 5, serial dilutions of cCLB8 or cSF25 (an isotype matched irrelevant Mab) were preincubated with IL-6sR and IL-1β and then cultured with HepG2 cells for 24 hours. Cell supernatant was then analyzed for Serum amyloid A production levels by ELISA. (Human SAA ELISA kit, Biosource, performed according to manufacturer's instructions). Error bars indicate SEM of duplicate samples. The data in FIG. 5 indicate that cCLB8 was able to inhibit IL-1β/IL-6 induced SAA production from HepG2 cells in a dose dependent manner.

Inhibition of IL-6 Induced Cell Proliferation by cCLB8 Mab

The murine B myeloma cell line, 7TD1, is induced to proliferate in the presence of IL-6. To demonstrate the ability of cCLB8 Mab to neutralize the activity of IL-6, the cells were incubated at 37° C. for 72 hours in IMDM containing 10% FBS and 0.5 ng/mL recombinant human IL-6 (R&D Systems), and with serial dilutions of cCLB8 Mab or negative control Mab 17-1A. Cell proliferation was measured by a luminescent ATP assay (ATPLite, Packard Bioscience) which correlates directly with cell number.

Figure 6:
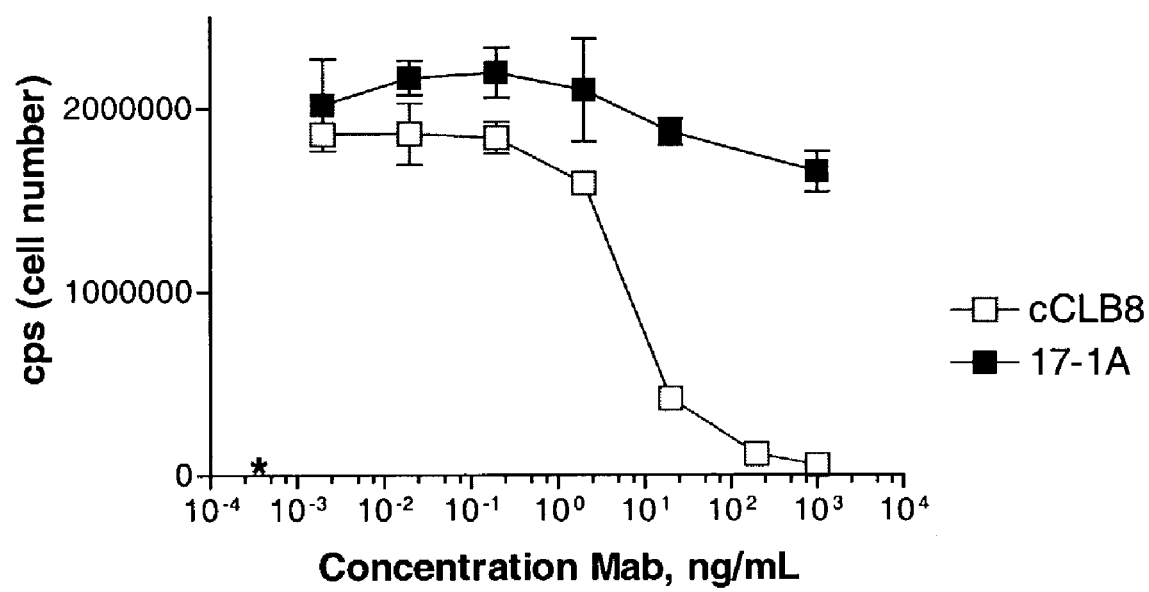
FIG. 6: Graph showing the ability of cCLB8 to neutralize rhIL-6-induced cell proliferation.

The data shown in FIG. 6 demonstrate that IL-6 dramatically stimulates proliferation of 7TD1 cells and cCLB8 inhibited this cell proliferation in a concentration dependent manner with an $EC_{50}$ of 7.2 ng/mL. Error bars indicate the SEM of duplicate samples. *represents proliferation of cells in the absence of rIL-6.

EXAMPLE 5

Epitope Mapping

The epitopes of several neutralizing anti IL-6 Mabs including CLB8 have been characterized using antibody binding to human IL-6 mutant proteins as described in (Brakenhoff, J. et al. (1990) J. Immunology 145: 561–568). Amino and carboxyl-terminal deletion mutants were prepared and the panel of antibodies to IL-6 was analyzed by antibody competition experiments. On the basis of the competition studies the neutralizing Mabs were divided into 2 groups (I and II). In this method, residues included in the epitope of a given Mab are delineated by its failure to recognize the corresponding site-specific single amino acid substitution variants of the antigenic protein. CLB.IL-6/8 was mapped to site I on the human IL-6 molecule which is composed of amino acids Gln29-Leu34 in close proximity of the carboxyl terminus of the molecule. Further studies (Kalai, M, et al., Eur. J. Biochem. 249, 690–700 (1997))

showed that CLB. IL-6/8 recognized amino acid residues crucial for the binding of IL-6 to the IL-6R (gp80). These studies also indicated that its epitope covers the ends of both the AB loop and the D helix regions of the IL-6 molecule.

EXAMPLE 6

In Vivo Characterization

Figure 7:
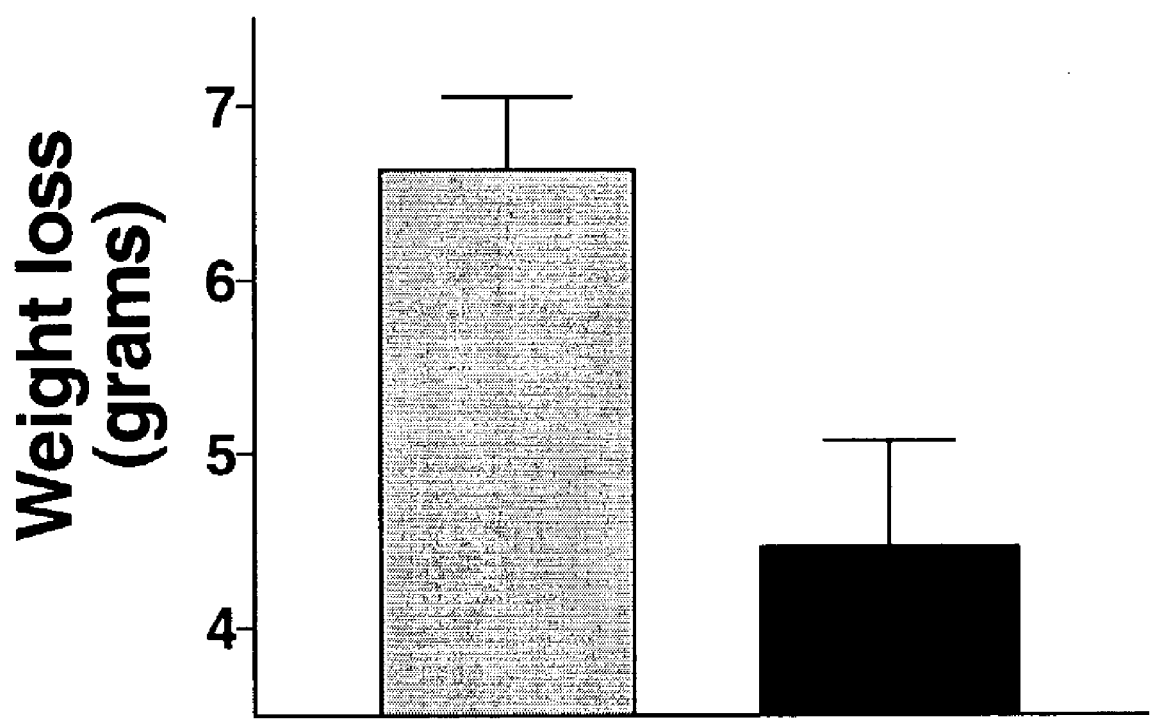
FIG. 7: Graph showing the relative reduction in host body weight loss in human tumor bearing mice treated with both anti-human and anti-mouse IL-6 antibodies.

Treatment with Anti-Human IL-6 (cCLB8) and Anti-Mouse IL-6 Mouse Mabs Delays Cancer Cachexia Human melanoma cells (A375S2) were inoculated into female nude mice and Mab therapy was initiated on the same day. Antibodies were injected intraperitoneally at a dose of 10 mg/kg (2×/week) and C57 (anti-CMV) was used as a control mAb. Combination of cCLB8 (anti-human IL-6) and MP520F3 (Mab to mouse IL-6, R&D Systems) were used to create a combined blockade significantly inhibited weight loss of human melanoma tumor bearing animals compared to control antibody C57 treated animals (FIG. 7). Antibody therapy did not effect tumor growth or final tumor weight. These findings indicate that IL6 participates in tumor-induced animal weight loss, and blockade of IL-6 can delay cancer cachexia in this model.

FIG. 7. Combined blockade of human and mouse IL6 (anti-IL6 mAbs cCLB8 and MP520F3) results in significant inhibition of animal weight loss. Corrected animal weight loss on Y axis is (animal weight-tumor weight at the end of the study) minus animal weight at start of the study. Each bar is the mean of data from at least 14 animals/group and error bars indicate standard deviation. A two tailed t-test analysis indicated that the anti-IL-6 group significantly inhibited body weight loss with p=0.007.

EXAMPLE 7

Affinity Measurements

BIAcore 2000, Sensor Chip CM-5 (gold surface on chip covered with a carboxymethylated dextran matrix), HBS (10 mM HEPES with 0.15 M NaCl, 3.4 mM EDTA, and 0.05% surfactant P20 at pH 7.4), amine coupling reagents (N-hydroxysuccinimde (NHS), N-ethyl-N'-(3-methylaminopropyl)-carbodimiide (EDC) and 1M ethanolamine HCl) were obtained from BIAcore and prepared according to the manufacturer's instructions. Anti-human Fc (Jackson AffiniPure Goat anti-human IgG, Fc□, Cat# 109-005-098, Lot#48646) was purchased from Jackson ImmunoResearch.

Chimeric CLB8 (Lot# PD1F03) IgG monoclonal antibody in 5 ml of 0.15M Sodium Chloride, 0.01M Sodium Phosphate, pH 7.2 was manufactured by Centocor. Recombinant Human IL-6 (Lot# A1197111) was purchased from R&D Systems.

An anti-human Fc (1.8 mg/ml) was diluted to a concentration of 50 µg/ml in NaOAc buffer (10 mM, pH 4.8) and coupled to the carboxymethylated dextran matrix of a CM-5 sensor chip using the manufacturer's amine-coupling chemistry as described in the BIAcore systems manual. Using the surface preparation wizard aiming for 10000 RU, the carboxyl groups on the sensor surfaces were first activated with NHS/EDC followed by the addition of the anti-human Fc. The remaining activated groups were blocked by the injection of 1M ethanolamine. Each of the flow cells was coupled individually. Employing these conditions, the four flow cell surfaces containing 7554–9571 resonance units (RU) of anti-human Fc were prepared. In preliminary experiments, it was determined that three injections (15 ul at 30 µl/min) 100 mM H3PO4/0.05% CHAPS would efficiently remove the bound immunoglobulin and preserve the binding capacity of the immobilized anti-human Fc.

Two experiments were performed on the BIAcore 2000 at 25° C. and a flow rate of 30 µL/min. cCLB8 was dissolved in HBS at 5 ug/ml. The analyte, IL-6, was dissolved in HBS at 0.25, 0.125, 0.062, 0.031, and 0.015 µg/ml. A designated amount of antibody was flowed over its respective flow cell followed by injections of 30 µl of each IL-6 concentration at 30 µl/min (association phase) and an uninterrupted 800 seconds of buffer flow (dissociation phase). The surface of the chip was regenerated by three sequential injections of 15 µl each with 100 mM H3PO4/0.05% CHAPS. The injections of HBS serve as a reference (blank sensogram) for the subtraction of bulk refractive indices for analysis. Using the 1:1 model in BIAanalysis 3.0, a local fit was done for both dissociation (kd, [s−1] and association (ka, [M−1s−1]) and the dissociation constant (KD, [M]) calculated (kd/ka).

Analysis was done using BIAevaluation version 3.0. Kinetic constants were derived from sensogram data by fitting the experimental curves to the rate equations derived from models of the interaction mechanism. A global analysis using a 1:1 binding model with local RUmax fit, the ka, kd, KD were determined (Table 1).

TABLE 1

Affinity Measurements for cCLB8 Mab by Biacore

| Sample | $k_a$ $(m^{-1}s^{-1})(\times 10^6)$ | $k_d$ $(s^{-1})$ $(\times 10^{-5})$ | $K_D(M)$ $(\times 10^{-11})$ | $Chi^2$ |
|---|---|---|---|---|
| cCLB8 | 1.1 | 6.2 | 5.7 | 0.111 |
| cCLB8 | 0.37 | 5.2 | 14 | 0.236 |

EXAMPLE 8

Anti-Idiotype Antibodies

Development of effective assay systems (immunohistochemistry and serum detection) for cCLB8 requires the use of anti-idiotypic antibodies. Therefore Balb/c mice are immunized with cCLB8 to generate anti-idiotypic antibodies to cCLB8 that may be utilized as pharmacokinetic probes in serum detection and immunohistochemical assays.

Immunization

Five Balb/c mice (Charles River Laboratories) at 6–7 weeks of age were immunized over a 12-week period with cCLB8 (Centocor, PD1F03) given at 50 µg IP and 25 µg SC. Each mouse received IP and SC injections. Injections occurred at 2-week intervals throughout the immunization regimen. Injection material administered IP was emulsified with an equal volume of Freund's Adjuvant (Sigma). The first IP injection utilized Completed Freund's Adjuvant in a total volume of 200 µl. Subsequent IP injections contained Incomplete Freund's Adjuvant. Injection material administered SC was diluted in PBS and divided between two injection sites at 100 µl/site. The mice were bled on days 0, 21, 47, and 77. Blood collections were performed on anesthetized mice by retro-orbital puncture, and serum was collected for titer determination by cCLB8 solid phase EIA. Three weeks following the end of the immunization protocol, Mouse #1 received a final IV booster injection of 100 µg cCLB8 diluted in 125 µl PBS.

Generation of Mouse cCLB8 Anti-Idiotypic Monoclonal Antibodies

One fusion utilizing a cCLB8 immunized Balb/c mouse spleen resulted in identification of 7 anti-id antibodies specific for cCLB8 via EIA. The 7 anti-id antibodies were shown not to bind other mouse/human chimeric antibodies such as C207A, C128A, C168J, C116J, C300A, and C301A. Six of the seven antibodies were of isotype IgG1κ and one antibody was IgG2bκ. Table 1 summarizes the results of the fusion. It should be noted that a maximum serum titer of 1:800 was achieved in the mouse after 47 days and remained constant throughout the duration of immunization.

Isotyping

Isotype determination of the antibodies was accomplished by use of Mouse Monoclonal Antibody Isotyping Kit (Life Technologies) in dipstick format. A mixture of dilution buffer, hybridoma supernatant, and Rat anti-mouse conjugate were incubated overnight at RT with shaking in tubes containing sticks pre-coated with various capture murine antibody isotypes. Sticks were removed from tubes, rinsed gently in dH$_2$O, and isotypes determined.

TABLE 1

Properties of Mouse cCLB8 anti-idiotypic Monoclonal Antibodies

| C code | Isotype |
| --- | --- |
| C433A | IgG1κ |
| C434A | IgG1κ |
| C435A | IgG1κ |
| C436A | IgG2bκ |
| C437A | IgG1κ |
| C438A | IgG1κ |
| C439A | IgG1κ |

Serum Inhibition Assays

Figure 8:
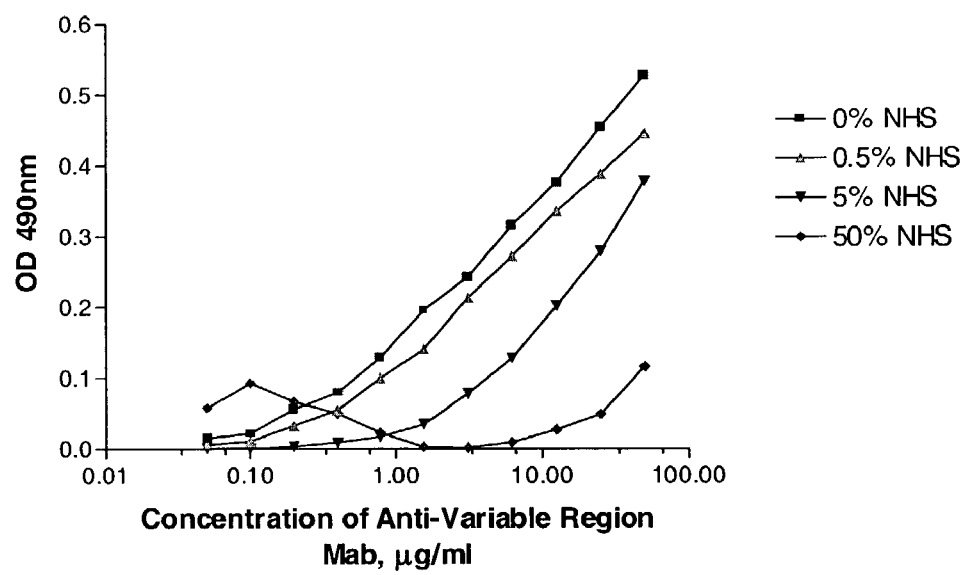
FIG. 8A–G: Graph showing the serum inhibition study profiles of 7 anti-idiotype antibodies.
Figure 8:
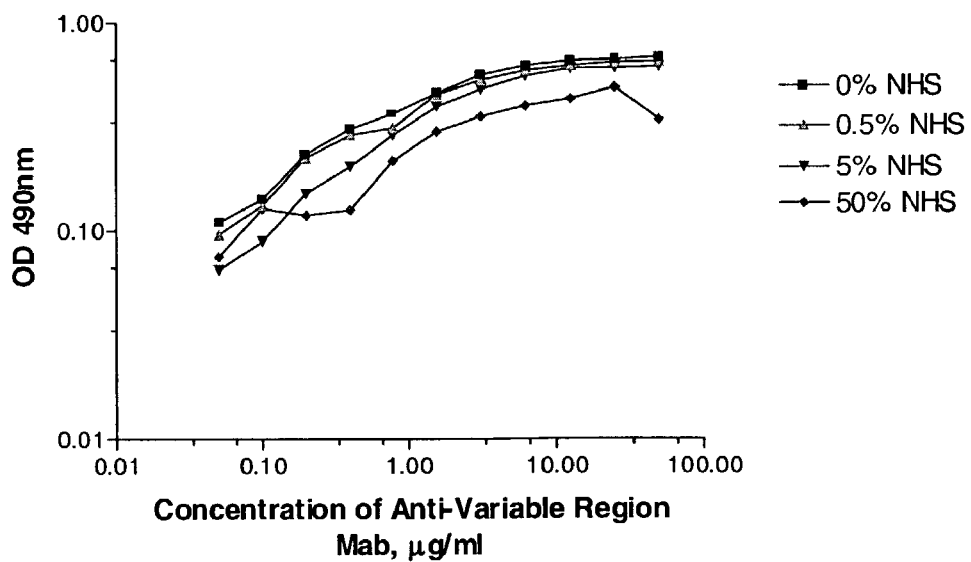
Figure 10:
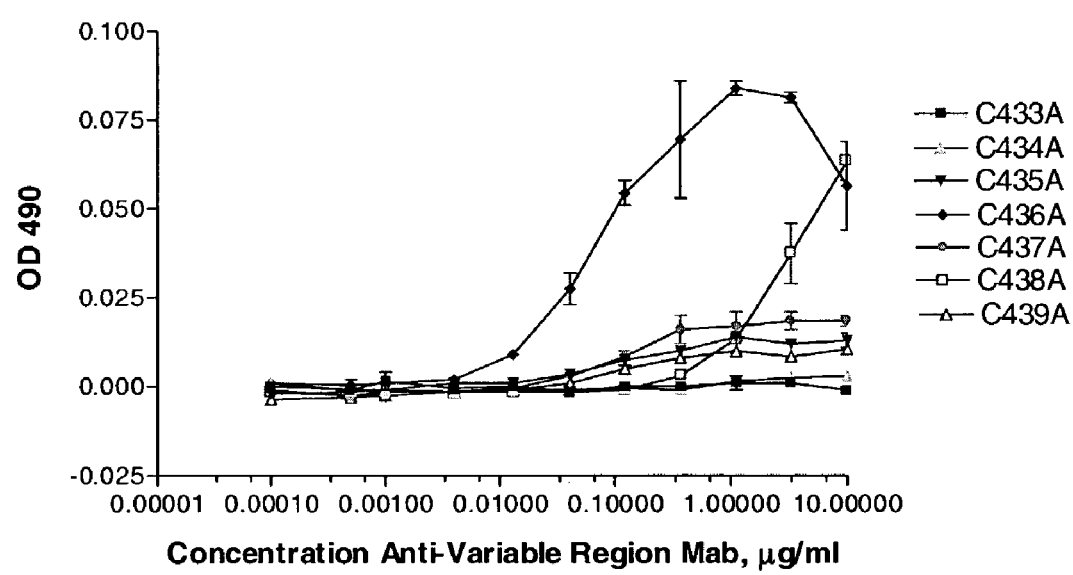
FIG. 10: Graph showing the anti-id binding to cCLB-8 pre-bound to human IL-6.

The effect of pooled normal human serum (NHS) on the 7 anti-id antibodies' ability to bind cCLB8 was determined. Doubling dilutions of Anti-id Mabs starting at 50 µg/ml were incubated in the presence of 0%, 0.5%, 5%, and 50% NHS for 30 minutes at 37° C. The mixtures were transferred to cCLB8 coated plates and incubated for 30 minutes at 37° C. Plates were washed then probed with goat anti-mouse IgG Fc*HRP. None of the anti-id Mabs were prevented from binding cCLB8 by 0% and 0.5% NHS. Three Mabs (C433A, C435A, and C437A) exhibited partial binding inhibition by 5% NHS. All except C434A and C436A were significantly affected by NHS concentration of 50% (FIGS. 8 A–G).

Inhibition of cCLB8 Binding to HuIL-6 by Anti-Id Mabs

The capability of the 7 anti-id antibodies to inhibit cCLB8 binding to HuIL-6 was assessed. Previous EIA studies have shown that cCLB8 binds very weakly to HuIL-6 coated plates. Two Mabs (C435A and C437A) at concentration excesses of 6–25 fold demonstrated virtually complete inhibition of cCLB8 binding to HuIL-6. C434A expressed an inhibitory effect for cCLB8 only at 25-fold excess. The two best antibodies at inhibiting binding of cCLB8 to HuIL-6 were C436A and C439A. These two antibodies were able to completely inhibit cCLB8 binding over an excess concentration range of 3 to 25 fold. C433A and C438A showed no inhibitory activity (FIG. 9). This assay confirmed the results obtained in a preliminary study.

Anti-Id Binding to cCLB8 Pre-Bound to HuIL-6

The capacity of the 7 anti-id antibodies to bind cCLB8 that was pre-bound to HuIL-6 was examined. cCLB8 at 10 µg/ml incubated on HuIL-6 plates for 30 minutes at 37° C. Plates were washed then incubated with tripling dilutions of Anti-id Mabs starting at 10 µg/ml for 30 minutes at 37° C. Plates were washed then probed with goat anti-mouse IgG Fc*HRP. As in preliminary studies, C436A and C438A were the only antibodies able to bind cCLB8 that was pre-bound to HuIL-6. FIG. 10 illustrates the binding abilities of the 7 anti-id antibodies for cCLB8 that is pre-bound to HuIL-6.

In summary, seven monoclonal anti-idiotypic antibodies were produced from fusion of murine myeloma cells and spleen cells from a Balb/c mouse immunized with chimeric anti-Human IL-6 antibody (cCLB8). Five of the anti-id antibodies (C434A, C435A, C436A, C437A, and C439A) were able to block cCLB8 binding to HuIL-6. Two antibodies (C436A and C438A) possessed the ability to bind cCLB8 that was pre-bound to HuIL-6, and two antibodies (C434A and C436A) were virtually unaffected from binding cCLB8 by any concentration of NHS tested. The broad binding profiles of these cCLB8 anti-idiotypic antibodies make some of them potential candidates for use as pharmacokinetic probes in serum detection and immunohistochemical assays.

It will be clear that the invention can be practiced otherwise than as particularly described in the foregoing description and examples.

Numerous modifications and variations of the present invention are possible in light of the above teachings and, therefore, are within the scope of the appended claims.

What is claimed is:

1. Isolated nucleic acid molecules encoding an antibody or antigen-binding fragment thereof that binds and inhibits the activity of human IL-6, wherein said antibody or antigen-binding fragment comprise:

a human antibody heavy chain constant region and a heavy chain variable region comprising CDR1, CDR2 and CDR3, which comprise the amino acid sequences SEQ ID NO: 1, SEQ ID NO:2 and SEQ ID NO:3, respectively; and a human antibody light chain constant region and a light chain variable region comprising CDR1, CDR2 and CDR3, which comprise the amino acid sequences SEQ ID NO:4, SEQ ID NO:5 and SEQ ID NO:6, respectively.

2. The isolated nucleic acid molecules of claim 1, wherein said isolated nucleic acid molecules comprise: a nucleotide sequence that encodes a human antibody heavy chain constant region and a heavy chain variable region comprising SEQ ID NO:7; and a nucleotide sequence that encodes a human antibody light chain constant region and a light chain variable region comprising SEQ ID NO:8.

3. A method for producing an IL-6 antibody or antigen-binding fragment, therof, comprising translating the nucleic acid molecules according to claim 1 under conditions in vitro, in vivo or in situ, such that the IL-6 antibody or antibody fragment is expressed in detectable or recoverable amounts.

4. A composition, comprising the nucleic acid molecules according to claim 1 and a carrier or diluent.

5. A method for producing an IL-6 antibody or antigen-binding fragment comprising transforming a host cell capable of expressing said antibody or antigen-binding fragment therof in recoverable amounts with the nucleic acid molecules according to claim 1 and expressing said antibody or antigen-binding fragment therof from said host cell.

6. The method according to claim 5 wherein said host cell is a mammalian cell, a plant cell or a yeast cell.

7. A vector, comprising the nucleic acid molecule according to claim 1.

8. The vector according to claim 7, wherein said vector comprises at least one promoter selected from the group consisting of a late or early SV490 promoter, a CMV promoter, an HSV tk promoter, a pgk (phosphoglycerate kinase) promoter, a human immunoglobulin promoter and an F-1 alpha promoter.

9. The vector according to claim 7, wherein said vector comprises at least one gene or portion thereof selected from the group consisting of methotrexate (MTX), green fluorescent prototein (GFP), dihydrofolate reductase (DHFR), neomycin (G418), and glutamine synthestase (GS).

* * * * *

UNITED STATES PATENT AND TRADEMARK OFFICE
CERTIFICATE OF CORRECTION

PATENT NO. : 7,291,721 B2  Page 1 of 1
APPLICATION NO. : 10/280716
DATED : November 6, 2007
INVENTOR(S) : Jill Giles-Komar et al.

It is certified that error appears in the above-identified patent and that said Letters Patent is hereby corrected as shown below:

Claim 1, Column 61, line 56, delete "comprise" and insert --comprises--;

Claim 3, Column 62, line 58, delete ", therof" and insert --thereof--;

Claim 5, Column 62, line 66, insert --thereof-- between "fragment" and "comprising";

Claim 5, Column 63, line 1, delete "therof" and insert --thereof--;

Claim 5, Column 63, line 3, delete "therof" and insert --thereof--;

Claim 7, Column 63, line 6, delete "molecule" and insert --molecules--;

Claim 9, Column 64, line 7, delete "prototein" and insert --protein--;

Claim 9, Column 64, line 8, delete "synthestase" and insert --synthetase--.

Signed and Sealed this

Twenty-seventh Day of January, 2009

JOHN DOLL
*Acting Director of the United States Patent and Trademark Office*

SEQUENCE LISTING

```
<160> NUMBER OF SEQ ID NOS: 16

<210> SEQ ID NO 1
<211> LENGTH: 5
<212> TYPE: PRT
<213> ORGANISM: Mus musculus

<400> SEQUENCE: 1

Ser Phe Ala Met Ser
1               5

<210> SEQ ID NO 2
<211> LENGTH: 17
<212> TYPE: PRT
<213> ORGANISM: Mus musculus
```

-continued

```
<400> SEQUENCE: 2

Glu Ile Ser Ser Gly Gly Ser Tyr Thr Tyr Tyr Pro Asp Thr Val Thr
1               5                   10                  15
Gly

<210> SEQ ID NO 3
<211> LENGTH: 10
<212> TYPE: PRT
<213> ORGANISM: Mus musculus

<400> SEQUENCE: 3

Gly Leu Trp Gly Tyr Tyr Ala Leu Asp Tyr
1               5                   10

<210> SEQ ID NO 4
<211> LENGTH: 10
<212> TYPE: PRT
<213> ORGANISM: Mus musculus

<400> SEQUENCE: 4

Ser Ala Ser Ser Ser Val Ser Tyr Met Tyr
1               5                   10

<210> SEQ ID NO 5
<211> LENGTH: 7
<212> TYPE: PRT
<213> ORGANISM: Mus musculus

<400> SEQUENCE: 5

Asp Thr Ser Asn Leu Ala Ser
1               5

<210> SEQ ID NO 6
<211> LENGTH: 9
<212> TYPE: PRT
<213> ORGANISM: Mus musculus

<400> SEQUENCE: 6

Gln Gln Trp Ser Gly Tyr Pro Tyr Thr
1               5

<210> SEQ ID NO 7
<211> LENGTH: 119
<212> TYPE: PRT
<213> ORGANISM: Mus musculus

<400> SEQUENCE: 7

Glu Val Gln Leu Val Glu Ser Gly Gly Lys Leu Leu Lys Pro Gly Gly
1               5                   10                  15

Ser Leu Lys Leu Ser Cys Ala Ala Ser Gly Phe Thr Phe Ser Ser Phe
            20                  25                  30

Ala Met Ser Trp Phe Arg Gln Ser Pro Glu Lys Arg Leu Glu Trp Val
        35                  40                  45

Ala Glu Ile Ser Ser Gly Gly Ser Tyr Thr Tyr Tyr Pro Asp Thr Val
    50                  55                  60

Thr Gly Arg Phe Thr Ile Ser Arg Asp Asn Ala Lys Asn Thr Leu Tyr
65                  70                  75                  80

Leu Glu Met Ser Ser Leu Arg Ser Glu Asp Thr Ala Met Tyr Tyr Cys
                85                  90                  95

Ala Arg Gly Leu Trp Gly Tyr Tyr Ala Leu Asp Tyr Trp Gly Gln Gly
```

```
                        100                 105                 110
Thr Ser Val Thr Val Ser Ser
            115

<210> SEQ ID NO 8
<211> LENGTH: 106
<212> TYPE: PRT
<213> ORGANISM: Mus musculus

<400> SEQUENCE: 8

Gln Ile Val Leu Ile Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Tyr Trp Tyr Gln Gln Lys Pro Gly Ser Ser Pro Arg Leu Leu Ile Tyr
            35                  40                  45

Asp Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Gly Tyr Pro Tyr Thr
                85                  90                  95

Phe Gly Gly Gly Thr Lys Leu Glu Ile Lys
            100                 105

<210> SEQ ID NO 9
<211> LENGTH: 15
<212> TYPE: DNA
<213> ORGANISM: Mus musculus

<400> SEQUENCE: 9
agctttgcca tgtct                                                      15

<210> SEQ ID NO 10
<211> LENGTH: 51
<212> TYPE: DNA
<213> ORGANISM: Mus musculus

<400> SEQUENCE: 10
gaaattagta gtggtgggag ttacacctac tatcctgaca ctgtgacggg c              51

<210> SEQ ID NO 11
<211> LENGTH: 30
<212> TYPE: DNA
<213> ORGANISM: Mus musculus

<400> SEQUENCE: 11
ggtttatggg ggtactatgc tcttgactac                                      30

<210> SEQ ID NO 12
<211> LENGTH: 30
<212> TYPE: DNA
<213> ORGANISM: Mus musculus

<400> SEQUENCE: 12
agtgccagct caagtgtaag ttacatgtac                                      30

<210> SEQ ID NO 13
<211> LENGTH: 21
<212> TYPE: DNA
<213> ORGANISM: Mus musculus
```

```
<400> SEQUENCE: 13
gacacatcca acctggcttc t                                                      21

<210> SEQ ID NO 14
<211> LENGTH: 27
<212> TYPE: DNA
<213> ORGANISM: Mus musculus

<400> SEQUENCE: 14
cagcagtgga gtggttaccc atacacg                                                27

<210> SEQ ID NO 15
<211> LENGTH: 357
<212> TYPE: DNA
<213> ORGANISM: Mus musculus

<400> SEQUENCE: 15
gaggtgcaac tggtggaatc tggaggaaaa ttactgaagc ctggagggtc cctgaaactc            60
tcctgtgcag cctctggatt caccttcagt agctttgcca tgtcttggtt tcgccagtct           120
ccagagaaga ggctggagtg ggtcgcagaa attagtagtg gtgggagtta cacctactat           180
cctgacactg tgacgggccg attcaccatc tccagagaca atgccaagaa cacctgtac            240 ctggaaatga gcagtctgag gtctgaggac acggccatgt attattgtgc aagggttta            300 tgggggtact atgctcttga ctactggggt caaggaacct cagtcaccgt ctcctca              357

<210> SEQ ID NO 16
<211> LENGTH: 318
<212> TYPE: DNA
<213> ORGANISM: Mus musculus

<400> SEQUENCE: 16
caaattgttc tcatacagtc tccagcaatc atgtctgcat ctccagggga gaaggtcacc            60
atgacctgca gtgccagctc aagtgtaagt tacatgtact ggtaccagca gaagccagga          120
tcctccccca gactcctgat ttatgacaca tccaacctgg cttctggagt ccctgttcgc          180
ttcagtggca gtgggtctgg gacctcttac tctctcacaa tcagccgaat ggaggctgag          240
gatgctgcca cttattactg ccagcagtgg agtggttacc catacacgtt cggagggggg          300
accaagctgg aaataaaa                                                        318
```